United States Patent
Morriss

(10) Patent No.: US 9,615,775 B2
(45) Date of Patent: Apr. 11, 2017

(54) METHODS AND DEVICES FOR OSTIUM MEASUREMENTS

(75) Inventor: John Morriss, San Francisco, CA (US)

(73) Assignee: Acclarent, Inc., Irvine, CA (US)

( * ) Notice: Subject to any disclaimer, the term of this patent is extended or adjusted under 35 U.S.C. 154(b) by 829 days.

(21) Appl. No.: 13/353,192

(22) Filed: Jan. 18, 2012

(65) Prior Publication Data

US 2012/0116254 A1    May 10, 2012

Related U.S. Application Data

(62) Division of application No. 11/799,459, filed on Apr. 30, 2007, now Pat. No. 8,118,757.

(51) Int. Cl.
*A61B 5/107* (2006.01)
*A61B 5/00* (2006.01)

(52) U.S. Cl.
CPC ............ *A61B 5/1076* (2013.01); *A61B 5/411* (2013.01)

(58) Field of Classification Search
USPC ........................................................ 600/587
See application file for complete search history.

(56) References Cited

U.S. PATENT DOCUMENTS

| 446,173 A | 2/1891 | Hancock |
| 504,424 A | 9/1893 | De Pezzer |
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robison |
| 2,493,326 A | 1/1950 | Trinder |

(Continued)

FOREIGN PATENT DOCUMENTS

| CH | 668188 | 12/1988 |
| CN | 2151720 | 1/1994 |

(Continued)

OTHER PUBLICATIONS

Argon Medical. Maxxim Medical. Ad for Sniper EliteTM Hydrophilic Ni-Ti Alloy Guidewire (2001).

(Continued)

*Primary Examiner* — Michael C Stout
(74) *Attorney, Agent, or Firm* — Frost Brown Todd LLC

(57) ABSTRACT

Devices and methods for accurately determining the size of an ostium of a patient and in particular sinus ostium. Methods for measuring a target ostium comprise inserting the distal end portion of an ostium measuring device into a patient, locating the target ostium with the measuring device, positioning the distal end portion of the measuring device appropriately adjacent to or into the target ostium and determining the diameter(s) of the target ostium by comparing the length, diameter and/or the circumference of the portion of the distal end portion of the measuring device adjacent to or within the target ostium.

27 Claims, 7 Drawing Sheets

(56) References Cited

U.S. PATENT DOCUMENTS

| | | |
|---|---|---|
| 2,847,997 A | 8/1958 | Tibone |
| 2,899,227 A | 8/1959 | Gschwend |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita et al. |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandoninck |
| 5,090,910 A | 2/1992 | Narlo |
| 5,112,228 A | 5/1992 | Zouras |
| 5,116,311 A * | 5/1992 | Lofstedt .................. 604/516 |
| 5,127,393 A | 7/1992 | McFarlin et al. |
| 5,137,517 A | 8/1992 | Loney et al. |

(56) References Cited

U.S. PATENT DOCUMENTS

| | | | |
|---|---|---|---|
| 5,139,510 | A | 8/1992 | Goldsmith, III et al. |
| 5,139,832 | A | 8/1992 | Hayashi et al. |
| D329,496 | S | 9/1992 | Wotton |
| 5,152,747 | A | 10/1992 | Olivier |
| 5,156,595 | A | 10/1992 | Adams |
| 5,163,989 | A | 11/1992 | Campbell et al. |
| 5,167,220 | A | 12/1992 | Brown |
| 5,168,864 | A | 12/1992 | Shockey |
| 5,169,043 | A | 12/1992 | Catania |
| 5,169,386 | A | 12/1992 | Becker et al. |
| 5,171,233 | A | 12/1992 | Amplatz et al. |
| 5,180,368 | A | 1/1993 | Garrison |
| 5,183,470 | A | 2/1993 | Wettermann |
| 5,189,110 | A | 2/1993 | Ikematu et al. |
| 5,195,168 | A | 3/1993 | Yong |
| 5,197,457 | A | 3/1993 | Adair |
| 5,207,695 | A | 5/1993 | Trout, III |
| 5,211,952 | A | 5/1993 | Spicer et al. |
| 5,215,105 | A | 6/1993 | Kizelshteyn et al. |
| 5,221,260 | A | 6/1993 | Burns et al. |
| 5,226,302 | A | 7/1993 | Anderson |
| 5,230,348 | A | 7/1993 | Ishibe et al. |
| 5,236,422 | A | 8/1993 | Eplett, Jr. |
| 5,243,996 | A | 9/1993 | Hall |
| D340,111 | S | 10/1993 | Yoshikawa |
| 5,250,059 | A | 10/1993 | Andreas et al. |
| 5,251,092 | A | 10/1993 | Brady et al. |
| 5,252,183 | A | 10/1993 | Shaban et al. |
| 5,255,679 | A | 10/1993 | Imran |
| 5,256,144 | A | 10/1993 | Kraus et al. |
| 5,263,926 | A | 11/1993 | Wilk |
| 5,264,260 | A | 11/1993 | Saab |
| 5,267,965 | A | 12/1993 | Deniega |
| 5,270,086 | A | 12/1993 | Hamlin |
| 5,273,052 | A | 12/1993 | Kraus et al. |
| 5,275,593 | A | 1/1994 | Easley et al. |
| 5,286,254 | A | 2/1994 | Shapland et al. |
| 5,290,310 | A | 3/1994 | Makower et al. |
| 5,295,694 | A | 3/1994 | Levin |
| 5,300,085 | A | 4/1994 | Yock |
| 5,304,123 | A | 4/1994 | Atala et al. |
| 5,308,326 | A | 5/1994 | Zimmon |
| 5,313,967 | A | 5/1994 | Lieber et al. |
| 5,314,417 | A | 5/1994 | Stephens et al. |
| 5,315,618 | A | 5/1994 | Yoshida |
| 5,324,306 | A | 6/1994 | Makower et al. |
| 5,333,620 | A | 8/1994 | Moutafis et al. |
| 5,334,167 | A | 8/1994 | Cocanower |
| 5,336,163 | A | 8/1994 | DeMane et al. |
| 5,341,818 | A | 8/1994 | Abrams et al. |
| 5,342,296 | A | 8/1994 | Persson et al. |
| 5,343,865 | A | 9/1994 | Gardineer et al. |
| 5,345,945 | A | 9/1994 | Hodgson et al. |
| 5,346,075 | A | 9/1994 | Nichols et al. |
| 5,346,508 | A | 9/1994 | Hastings |
| 5,348,537 | A | 9/1994 | Wiesner et al. |
| 5,350,396 | A | 9/1994 | Eliachar |
| 5,356,418 | A | 10/1994 | Shturman |
| 5,368,049 | A | 11/1994 | Raman et al. |
| 5,368,558 | A | 11/1994 | Nita |
| 5,368,566 | A | 11/1994 | Crocker |
| 5,372,138 | A | 12/1994 | Crowley et al. |
| 5,372,584 | A | 12/1994 | Zink et al. |
| D355,031 | S | 1/1995 | Yoshikawa |
| 5,386,817 | A | 2/1995 | Jones |
| 5,391,147 | A | 2/1995 | Imran et al. |
| 5,391,179 | A | 2/1995 | Mezzoli |
| 5,402,799 | A | 4/1995 | Colon et al. |
| 5,409,444 | A | 4/1995 | Kensey |
| 5,411,475 | A | 5/1995 | Atala et al. |
| 5,411,476 | A | 5/1995 | Abrams et al. |
| 5,411,477 | A | 5/1995 | Saab |
| 5,415,633 | A | 5/1995 | Lazarus |
| 5,425,370 | A | 6/1995 | Vilkomerson |
| 5,439,446 | A | 8/1995 | Barry |
| 5,441,494 | A | 8/1995 | Ortiz |
| 5,441,497 | A | 8/1995 | Narciso, Jr. |
| 5,450,853 | A | 9/1995 | Hastings et al. |
| 5,451,221 | A | 9/1995 | Cho et al. |
| 5,454,817 | A | 10/1995 | Katz |
| 5,458,572 | A | 10/1995 | Campbell et al. |
| 5,465,717 | A | 11/1995 | Imran et al. |
| 5,465,733 | A | 11/1995 | Hinohara et al. |
| 5,478,565 | A | 12/1995 | Geria |
| 5,486,181 | A | 1/1996 | Cohen et al. |
| 5,496,338 | A | 3/1996 | Miyagi et al. |
| 5,497,783 | A | 3/1996 | Urick et al. |
| 5,507,301 | A | 4/1996 | Wasicek et al. |
| 5,507,725 | A | 4/1996 | Savage et al. |
| 5,507,766 | A | 4/1996 | Kugo et al. |
| 5,512,055 | A | 4/1996 | Domb et al. |
| 5,514,128 | A | 5/1996 | Hillsman et al. |
| 5,519,532 | A | 5/1996 | Broome |
| 5,531,676 | A | 7/1996 | Edwards et al. |
| 5,533,985 | A | 7/1996 | Wong |
| 5,538,008 | A | 7/1996 | Crowe |
| 5,546,964 | A | 8/1996 | Stangerup |
| 5,549,542 | A | 8/1996 | Kovalcheck |
| 5,558,073 | A | 9/1996 | Pomeranz et al. |
| 5,558,652 | A | 9/1996 | Henke |
| 5,562,619 | A | 10/1996 | Mirarchi et al. |
| 5,568,809 | A | 10/1996 | Ben-Haim |
| 5,571,086 | A | 11/1996 | Kaplan et al. |
| 5,578,007 | A | 11/1996 | Imran |
| 5,578,048 | A | 11/1996 | Pasqualucci et al. |
| 5,584,827 | A | 12/1996 | Korteweg et al. |
| 5,591,194 | A | 1/1997 | Berthiaume |
| 5,599,284 | A | 2/1997 | Shea |
| 5,599,304 | A | 2/1997 | Shaari |
| 5,599,576 | A | 2/1997 | Opolski |
| 5,601,087 | A | 2/1997 | Gunderson et al. |
| 5,601,594 | A | 2/1997 | Best |
| 5,607,386 | A | 3/1997 | Flam |
| 5,617,870 | A | 4/1997 | Hastings et al. |
| 5,626,374 | A | 5/1997 | Kim, III |
| 5,633,000 | A | 5/1997 | Grossman et al. |
| 5,634,908 | A | 6/1997 | Loomas |
| 5,638,819 | A | 6/1997 | Manwaring et al. |
| 5,643,251 | A | 7/1997 | Hillsman et al. |
| 5,645,789 | A | 7/1997 | Roucher, Jr. |
| 5,647,361 | A | 7/1997 | Damadian |
| 5,656,030 | A | 8/1997 | Hunjan et al. |
| 5,662,674 | A | 9/1997 | Debbas |
| 5,664,567 | A | 9/1997 | Linder |
| 5,664,580 | A | 9/1997 | Erickson et al. |
| 5,665,052 | A | 9/1997 | Bullard |
| 5,669,388 | A | 9/1997 | Vilkomerson |
| 5,673,707 | A | 10/1997 | Chandrasekaran |
| 5,676,673 | A | 10/1997 | Ferre et al. |
| 5,679,400 | A | 10/1997 | Tuch |
| 5,682,199 | A | 10/1997 | Lankford |
| 5,685,838 | A | 11/1997 | Peters et al. |
| 5,685,847 | A | 11/1997 | Barry |
| 5,690,373 | A | 11/1997 | Luker |
| 5,693,065 | A | 12/1997 | Rains, III |
| 5,694,945 | A | 12/1997 | Ben-Haim |
| 5,697,159 | A | 12/1997 | Linden |
| 5,700,286 | A | 12/1997 | Tartaglia et al. |
| 5,707,389 | A | 1/1998 | Louw et al. |
| 5,708,175 | A | 1/1998 | Koyanagi et al. |
| 5,711,315 | A | 1/1998 | Jerusalmy |
| 5,713,839 | A | 2/1998 | Shea |
| 5,713,946 | A | 2/1998 | Ben-Haim |
| 5,718,702 | A | 2/1998 | Edwards |
| 5,720,300 | A | 2/1998 | Fagan et al. |
| 5,722,401 | A | 3/1998 | Pietroski et al. |
| 5,722,984 | A | 3/1998 | Fischell et al. |
| 5,729,129 | A | 3/1998 | Acker |
| 5,730,128 | A | 3/1998 | Pomeranz et al. |
| 5,733,248 | A | 3/1998 | Adams et al. |
| 5,752,513 | A | 5/1998 | Acker et al. |
| 5,762,604 | A | 6/1998 | Kieturakis |
| 5,766,158 | A | 6/1998 | Opolski |
| 5,775,327 | A | 7/1998 | Randolph et al. |

(56) References Cited

U.S. PATENT DOCUMENTS

| | | |
|---|---|---|
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelmayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,331,112 B1 * | 12/2001 | Lee ............................. 433/102 |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |

(56) References Cited

U.S. PATENT DOCUMENTS

| | | |
|---|---|---|
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,596,009 B1 | 7/2003 | Jelic |
| 6,607,546 B1 | 8/2003 | Murken |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,755,812 B2 | 6/2004 | Peterson et al. |
| 6,776,772 B1 | 8/2004 | dVrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,011,654 B2 | 3/2006 | Dubrul et al. |
| 7,022,105 B1 | 4/2006 | Edwards |
| 7,043,961 B2 | 5/2006 | Pandey et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,361,168 B2 | 4/2008 | Makower et al. |
| 7,366,562 B2 | 4/2008 | Dukesherer et al. |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,717,933 B2 | 5/2010 | Becker |
| 7,720,521 B2 | 5/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,799,048 B2 | 9/2010 | Hudson et al. |
| 7,803,150 B2 | 9/2010 | Chang et al. |
| 7,837,672 B2 | 11/2010 | Intoccia |
| D630,321 S | 1/2011 | Hamilton, Jr. |
| D632,791 S | 2/2011 | Murner |
| 7,988,705 B2 | 8/2011 | Galdonik et al. |
| 8,123,722 B2 | 2/2012 | Chang et al. |
| 8,197,552 B2 | 6/2012 | Mandpe |
| 2001/0004644 A1 | 6/2001 | Levin |

(56) References Cited

U.S. PATENT DOCUMENTS

| | | |
|---|---|---|
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 | 10/2001 | Malackowski et al. |
| 2001/0051761 A1 | 12/2001 | Khadem |
| 2001/0051802 A1 | 12/2001 | Woloszko et al. |
| 2002/0002349 A1 | 1/2002 | Flaherty et al. |
| 2002/0006961 A1 | 1/2002 | Katz et al. |
| 2002/0010384 A1 | 1/2002 | Shahidi et al. |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0038130 A1 | 3/2002 | Adams |
| 2002/0055746 A1 | 5/2002 | Burke et al. |
| 2002/0062133 A1 | 5/2002 | Gilson et al. |
| 2002/0077852 A1 | 6/2002 | Ford et al. |
| 2002/0082558 A1 | 6/2002 | Samson et al. |
| 2002/0082583 A1 | 6/2002 | Lerner |
| 2002/0090388 A1 | 7/2002 | Humes et al. |
| 2002/0103459 A1 | 8/2002 | Sparks et al. |
| 2002/0107475 A1 | 8/2002 | Maginot |
| 2002/0116011 A1 | 8/2002 | Chung et al. |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014008 A1 | 1/2003 | Jacques |
| 2003/0014036 A1 | 1/2003 | Varner et al. |
| 2003/0017111 A1 | 1/2003 | Rabito |
| 2003/0018291 A1 | 1/2003 | Hill et al. |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0109810 A1 | 6/2003 | Brennan et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0171650 A1 | 9/2003 | Tartaglia et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0209096 A1 | 11/2003 | Pandey et al. |
| 2003/0212446 A1 | 11/2003 | Kaplan et al. |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1 | 4/2004 | Becker |
| 2004/0097788 A1 | 5/2004 | Mourlas et al. |
| 2004/0098017 A1 | 5/2004 | Saab et al. |
| 2004/0102721 A1* | 5/2004 | McKinley ............ 600/587 |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |
| 2004/0181175 A1 | 9/2004 | Clayman et al. |
| 2004/0193073 A1 | 9/2004 | DeMello et al. |
| 2004/0193139 A1 | 9/2004 | Armstrong et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027249 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco et al. |
| 2005/0059931 A1 | 3/2005 | Garrison et al. |
| 2005/0089670 A1 | 4/2005 | Large et al. |
| 2005/0107720 A1 | 5/2005 | Burmeister et al. |
| 2005/0107738 A1 | 5/2005 | Slater et al. |
| 2005/0113686 A1 | 5/2005 | Peckham |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228260 A1 | 10/2005 | Burwell et al. |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0273132 A1 | 12/2005 | Shluzas et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1 | 1/2006 | Chang et al. |
| 2006/0004323 A1* | 1/2006 | Chang et al. .................... 604/28 |
| 2006/0063973 A1 | 3/2006 | Makower et al. |
| 2006/0064039 A1* | 3/2006 | Griego et al. ................ 600/587 |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0161255 A1 | 7/2006 | Zarowski et al. |
| 2006/0173291 A1 | 8/2006 | Glossop |
| 2006/0173382 A1 | 8/2006 | Schreiner |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0233036 A1 | 10/2007 | Mandpe |
| 2007/0249901 A1* | 10/2007 | Ohline et al. ................ 600/117 |
| 2007/0250050 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |

(56) References Cited

U.S. PATENT DOCUMENTS

| | | |
|---|---|---|
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0154345 A1 | 6/2008 | Taylor |
| 2008/0187098 A1 | 8/2008 | Gertner et al. |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0262508 A1 | 10/2008 | Clifford et al. |
| 2008/0262509 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088677 A1 | 4/2009 | Cohen |
| 2009/0088728 A1 | 4/2009 | Dollar et al. |
| 2009/0093823 A1 | 4/2009 | Chang et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0192492 A1 | 7/2009 | Eaton et al. |
| 2009/0198216 A1 | 8/2009 | Muni et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0087811 A1 | 4/2010 | Herrin et al. |
| 2010/0114066 A1 | 5/2010 | Makower et al. |
| 2010/0121308 A1 | 5/2010 | Muni et al. |
| 2010/0174308 A1 | 7/2010 | Chang et al. |
| 2010/0174366 A1 | 7/2010 | Avior |
| 2010/0198191 A1 | 8/2010 | Clifford et al. |
| 2010/0198302 A1 | 8/2010 | Shalev |
| 2010/0274188 A1 | 10/2010 | Chang et al. |
| 2010/0290244 A1 | 11/2010 | Nath |
| 2011/0166190 A1 | 7/2011 | Anderson et al. |

FOREIGN PATENT DOCUMENTS

| | | |
|---|---|---|
| CN | 2352818 | 12/1999 |
| DE | 03202878 | 8/1983 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0257605 | 3/1988 |
| EP | 0355996 | 2/1990 |
| EP | 0418391 | 3/1991 |
| EP | 0427852 | 5/1991 |
| EP | 0623582 | 11/1994 |
| EP | 0624349 | 11/1994 |
| EP | 0744400 | 11/1996 |
| EP | 0585757 | 6/1997 |
| EP | 0893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-067935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 96/29071 | 9/1996 |
| WO | WO 97/21461 | 6/1997 |
| WO | WO 99/24106 | 5/1999 |
| WO | WO 99/30655 | 6/1999 |
| WO | WO 99/32041 | 7/1999 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |

(56) References Cited

FOREIGN PATENT DOCUMENTS

| WO | WO 2008/051918 | 5/2008 |
|---|---|---|
| WO | WO 2008/134382 | 11/2008 |

OTHER PUBLICATIONS

Aust, R., et al 'The Functional Size of the Human Maxillary Ostium in Vivo' Acta. Otolaryn. (1978) vol. 78 pp. 432-435.
Baim, D.S., MD Grossman's Cardiac Catheterization, Angiography, and Intervention (2000) Lippincott Williams & Wilkins pp. 76, 84 & 214.
Barrett, S. 'Be Wary of Neurocranial Restructuring (NCR)' Chirobase (available at: http://www.chirobase.org/06DD/ncr.html) (Jul. 2003.).
Bartal, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. http://inventors.about.com/library/inventors/blcatheter.htm?p=1.
Benninger et al. Adult Chronic Rhinosinusitis: Definitions, Diagnosis, Epidemiology, and Pathophysiology' Arch Otolarygol Head and Neck Surg. (Sep. 2003) vol. 129 pp. S1-S32.
Bent et al. 'The Frontal Cell as a Cause of Frontal Sinus Obstruction' American Journal of Rhinology. (1994) vol. 8, No. 4 pp. 185.
Binner et al. 'Fibre-Optic Transillumination of the Sinuses: A Comparison of the Value of Radiography and Transillumination in Antral Disease' Clinical Otolaryngology. (1978) vol. 3 pp. 1-11.
Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Bumm, P., H. Kaiser et al 'Cortizontherapie, Corticoide in Klinik and Praxis' Thieme, Stuggart (1992) pp. 390-401 [Summary of textbook].
Casiano et al. 'Endoscopic Lothrop Procedure: The University of Miami Experience' American Journal of Rhinology (1998) vol. 12, No. 5 pp. 335-339.
Casserly, I.P. et al Chapter 7. 'Guides and Wires in Percutaneous Coronary Intervention' Strategic Approaches in Coronary Intervention (2006) Lippincott Williams & Wilkins pp. 91-99.
Chien, Y.W. et al. Nasal Systemic Drug Delivery, Drugs and the Pharmaceutical Sciences (1989) Marcel Dekker, Inc. Chapter 3, pp. 39-88.
Cohen et al 'Endoscopic Sinus Surgery: Where we are and where we're going' Current Opinion in Otolaryngology & Head and Neck Surgery (2005) vol. 13 pp. 32-38.
Colla, A. et al 'Trihaloacetylated Enol Ethers-General Synthetic Procedure and Heterocyclic Ring Closure Reactions with Hydroxylamine' Synthesis. (Jun. 1991) pp. 483-486.
Costa, M.N. et al 'Endoscopic Study of the Intranasal Ostium in External Dacryocystorhinostomy Postoperative. Influence of Saline Solution and 5- Flurorouracil' Clinics. (2007) vol. 62, Issue 1 pp. 41-46. http://www.scielo.br/scielo.php?pid=S1807-59322007000100007&script=sci_arttext.
Cussler, E.L. *Diffusion: Mass Transfer in Fluid Systems* Cambridge University Press (1996) [Summary of textbook].
Davis, G.E. et al., 'A Complication From Neurocranial Restructuring' Arch Otolaryngology Head Neck Surg. (Apr. 2003) vol. 129 pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al *Handbook of Biodegradable Polymers* Harwood Academic Publishers (1997) [Summary of textbook].

Draf, W. 'Endonasal Micro-Endoscopic Frontal Sinus Surgery: the Fulda Concept' Op Tech Otolaryngol Head Neck Surg. (1991) vol. 2 pp. 234-240.
Edmond et al 'ENT Surgical Stimulator' Nov. 1998 Final Report Cooperative Agreement No. DAMD17-95-2-5023.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54-55.
Feldman, R.L. et al 'New Steerable, Ultra-Low-Profile, Fixed Wire Angioplasty Catheter: Initial Experience With the Cordis Orion™ Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M. M.D., et al 'Frontal Sinus Surgery: Endoscopic Technique' Operative Techniques in Otolarynology-Head and Neck Surgery. (Jun. 2001) vol. 12, No. 2 pp. 60-65.
Friedman, et al 'Intraoperative and Postoperative Assessment of Frontal Sinus Patency by Transillumination' Laryngoscope. (Apr. 2000) vol. 110 pp. 683-684.
Friedman et al 'Middle Turbinate Medialization and Preservation in Endoscopic Surgery' Otolaryngol. Head Neck Surg. (2000) vol. 123, No. 1, Part 1. pp. 76-80.
Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.
Gatot, A. et al., 'Early Treatment of Orbital Floor Fractures with Catheter Balloon in Children' Int. J. Pediatric Otorhinolaryngol (1991) vol. 21 pp. 97-101.
Gerus, I.I. et al 'β-Ethoxyvinyl Polyfluroroalkyl Ketones-Versatile Synthones in Fluoroorganic Chemistry' Journal of Fluorine Chemistry. (1994) vol. 69 pp. 195-198. Elsevier Science S.A.
Good, R.H. 'An Intranasal Method for Opening the Frontal Sinus Establishing the Largest Possible Drainage' Laryngoscope. (1908) vol. 18 pp. 266-274.
Gopferich 'Polymer Degradation and Erosion: Mechanisms and Applications' Eur. J. Pharm. Biophar. (1996) vol. 42 pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.
Gottman, et al. 'Balloon Dilatation in the Nasal Cavity and Paranasal Sinuses' CIRSE. (Sep. 25, 2004) pp. 1-27.
Gottman, et al. 'Balloon Dilatation of Recurrent Ostial Occlusion of the Front Sinus' Abstract No. B-04353. European Congress of Radiology. (Mar. 2, 2001).
Gottman, et al. 'Successful Treatment of Recurrent Post-Operative Frontal Sinus Stenoses by Balloon Dilatation' CIRSE. (Oct. 5, 2002).
Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.
Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.
Hojo, M. et al 'Electrophilic Substitutions of Olefinic Hydrogens II. Acylation of Vinyl Ethers and N Vinyl Amides' Chemistry Letters (1976) pp. 499-502.
Hopf, J.U.G. et al 'Miniature Endoscopes in Otorhinolaryngologic Applications' Min Invas Ther & Allied Technol. (1998) vol. 7, No. 3 pp. 209-218.
Hosemann, W. et al *A Dissection Course on Endoscopic Endonasal Sinus Surgery* (2005) Endo-Press, Tuttlingen pp. 4-37.
Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.
Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.

(56) References Cited

OTHER PUBLICATIONS

Hosemann W.G. et al *Minimally Invasive Endonasal Sinus Surgery* Thieme, Stuttgart, New York (2000) [Summary of textbook].
Hosemann, M.E. et al 'Normal Wound Healing of the Paranasal Sinuses—Clinical and Experimental Investigators' Eur Arch Otorhinolarygol. (1991) vol. 248 pp. 390-394.
Hosemann, W. et al 'Weiterbehandlung nach Nasennebenhohleneingriffen, Part 2: Theapeutische Maßnahmen' HNO akutell 7 (1999) pp. 291-302.
Hospital Corpsman Sickcall Screener's Handbook. Naval Hospital Great Lakes (Apr. 1999) http://www.brooksidepress.org/Products/Operationa.Medicine/DATA. 2001 pp. 1-6.
Hybels, R.L. 'Transillumination During Osteoplastic Frontal Sinusotomy' the Laryngoscope (Sep. 1981) vol. 91 pp. 1560.
Ijaduola, T.G.A. 'Use of a Foley Catheter for Short-Term Drainage in Frontal Sinus Surgery' The Journal of Laryngology and Otology. (1989) vol. 103 pp. 375-378.
Ingals, F. 'New Operation and Instruments for Draining the Frontal Sinus' Ann. Otol Rhinol Laryngol. (1905) vol. 14 pp. 515-519.
Iro, H. et al 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. (1997) vol. 107 pp. 1-36.
Kennedy, D.W., M.D. et al *Diseases of the Sinuses Diagnosis and Management* (Copyright 2001) by B.C. Decker Inc.
Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.
Kingdom, T.T. et al 'Image-Guided Surgery of the Sinuses: Current Technology and Applications' Otolaryngol. Clin. North Am. (Apr. 2004) vol. 37, No. 2 pp. 381-400.
Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.
Kozlov et al 'Diagnosis and Treatment of Sinusitis by YAMIK Sinus Catheters' Rhinology (1996) vol. 34. pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery (1991) vol. 2, No. 4 pp. 226-231.
Laliberte F. et al 'Clinical and Pathologic Methods to Assess the Long-Term Safety or Nasal Corticosteroids' Allergy (2000) vol. 55, No. 8 pp. 718-722.
Lang, E.V. et al 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium. General Session Abstracts. (1993) Jul. 21-24.
Large, G.C. 'Crystalline Tetracycline Hydrochloride in the Treatment of Acute and Chronic Maxillary Sinusitis' Canad. M. A. J. (1958) vol. 79 pp. 15-16.
Lund, V.J. 'Maximal Medical Therapy for Chronic Rhinosinusitis' Otolaryngol Clin N Am. (2005) vol. 38 pp. 1301-1310.
Maran, A.G.D. et al 'The Use of the Foley Catheter in the Tripod Fracture' J. Laryngol. Otol (1971) vol. 85, Issue 9 pp. 897-902.
May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.
Medtronic, xomed.com-MicroFrance Catalog Browser. http://www.xomcat.com/xomfrance/index.php?zone=both&cat=18&sub=58&prodline=1272 (Dec. 31, 2003) pp. 1-2.
Mehan, V.K. et al 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron (2000) vol. 56 pp. 10067-10074. Elseview Science Ltd.
Metson, R. et al 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope (Jan. 1996) vol. 106, Issue 1, Supplement 77 pp. 1-18.
Miller et al. 'Management of Fractures of the Supraorbital Rim' Journal of Trauma (Jul. 1978) vol. 18, No. 7 pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.
Mols, B. 'Moveable Tool Tip for Keyhole Surgery' Delft Outlook (2005) vol. 3 pp. 13-17.
Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.
Park, K. et al *Biodegreadable Hydrogels for Medicinal Substance Delivery* (1993) Technomic Publishing Inc. Lancaster.
Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.
Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L. et al 'Balloon Technique for Treatment of Frontal Sinus Fractures' The Journal of Laryngology & Otology (1967), vol. 81. pp. 1157-1161.
Pownell, P.H. et al 'Diagnostic Nasal Endoscopy' Plastic & Reconstructive Surgery (1997) vol. 99, Iss. 5 pp. 1451-1458.
Prince et al 'Analysis of the Intranasal Distribution of Ointment' J Otolaryngol. (1997) vol. 26 pp. 357-360.
Ramsdale, D.R. *Illustrated Coronary Intervention A case- oriented approach* (2001) Martin Dunitz Ltd. pp. 1-5.
Ritter, F.N. et al *Atlas of Paranasal Sinus Surgery* (1991) Igaku-Shoin Medical Pub pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' TEXAS State Journal of Medicine. (May 1951) pp. 281-288.
Sama, A. et al 'Current Opinions on the Surgical Management of Frontal Sinus Disease' ENT News. www.pinpointmendical.com/ent-news (2009) vol. 17 No. 6 pp. 60-63.
Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.
*Sawbones Catalog* 2001, Pacific Research Laboratories, Inc., Vashon, Washington 98070 USA.
Saxon, R.R., et al 'Technical Aspects of Accessing the Portal Vein During the TIPS Procedure' J. Vasc. Interv. Radiol. (1997) vol. 8, No. 5 pp. 733-744.
Schaefer, S.D., M.D. *Rhinology and Sinus Disease A Problem-Oriented Approach* (Copyright 1988) by Mosby, Inc.
Schneider. Pfizer Ad for Softip [date of publication unknown].
Shah, N.J. et al 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at www.bhj.org/journal/1999_4104_oct99/sp_659.htm.
Single-Pole and Multi-Pole Lightguides for UV Spot Light Curing Systems. http://www.dymax.com/products/curing_equipment/lightguids/light. (2004) pp. 1-2.
Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.
St. Croix, et al 'Genes Expressed in Human Tumor Endothelium' Science (May 15, 2000) vol. 289 pp. 1197-1202.
Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.

(56) References Cited

OTHER PUBLICATIONS

Stammberger, et al 'Special Endoscopic Anatomy of the Lateral Nasal Wall and Ethmoidal Sinuses' Functional Endoscopic Sinus Surgery. (1991) Ch. 3, pp. 49-87.
Strohm et al 'Die Behandlung von Stenosen der oberen Luftwege mittels rontgenologisch gesteuerter Ballondilation (Sep. 25, 1999).
Strohm, et al 'Le Traitement Des Stenoses Voies Aeriennes Superieures Par Dilation Au Balloon' Sep. 25, 1999.
Strohm, et al 'Treatment of the Stenoses of the Upper Air Routes by Balloon Dilation' Sudwestdeutscher (Sep. 25, 1999) Abstract 45 pp. 1-3.
SurgTrainer Product Information 'Incisive Human Nasal Model for ESS Training' Surg Trainer, Ltd. Ibaraki, Japan (2004) http://www1.accsnet.ne.jp/~juliy/st/en/partslist.html.
Tabor, M.H. et al 'Symptomatic Bilateral Nasolacrimal Duct Cysts in a Newborn-Rhinoscopic Clinic' Ear, Nost & Throat Journal (2003) http://findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinolaringol. (1978) vol. 6 pp. 45-47.
Terumo. Medi-Tech. Boston Scientific. (1993) Ad for Glidewire.
The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4 [retrieved on Nov. 30, 2010]. Retrieved from the Internet.
Weber, R. et al 'Endonasale Stirnhohlenchirugie mit Langzeiteinlage eines Platzhalters' Laryngol. Rhinol. Otol. (1997) vol. 76 pp. 728-734. (English Abstract).
Weber, R. et al 'Videoendoscopic Analysis of Nasal Steroid Distribution' Rhinology (1999) vol. 37 pp. 69-73.
Weiner, R.I., D.O. et al 'Development and Application of Transseptal Left Heart Catheterization' Cathet. Cardiovasc. Diagn. (1988) vol. 15, No. 2 pp. 112-120.
Wiatrak, B.J. et al 'Unilateral Choanal Atresia: Initial Presentation and Endoscopic Repair' International Journal of Pediatric Otorhinolaryngology (1998) vol. 46 pp. 27-35.
Woog, et al. 'Paranasal Sinus Endoscopy and Orbital Fracture Repair' Arch Ophthalmol. (May 1998) vol. 116 pp. 688-691.
Wormald, P.J. et al 'The 'Swing-Door' Technique for Uncinectomy in Endoscopic Sinus Surgery' The Journal of Laryngology and Otology (1998) vol. 112 pp. 547-551.
Xomed-Treace. Bristol-Myers Squibb. Ad for Laser Shield II. Setting the Standards for Tomorrow [date of publication unknown].
Yamauchi, Y. et al 'Development of a Silicone Model for Endoscopic Sinus Surgery' proc International Journal of Computer Assisted Radiology and Surgery (1999) vol. 99 pp. 1039.
Yamauchi, Y. et al 'A Training System for Endoscopic Sinus Surgery with Skill Evaluation' Computer Assisted Radiology and Surgery (2001) with accompanying copy of poster presentation.
Yanagisawa et al 'Anterior and Posterior Fontanelles.' Ear, Nose & Throat Journal (2001) vol. 80. p. 10-12.
Zimarino, M., MD et al 'Initial Experience with the Europass™: A New Ultra-Low Profile Monorail Balloon Catheter' Cathet. Cardiovasc. Diagn. (1994) vol. 33, No. 1 pp. 76-79.
http://www.invotec.net/rhinology/ksplint.html. *K-Splint Internal Nasal Splints*; Jan. 25, 2007.
http://www.doylemedical.com/nasalsplints.htm; *Doyle Nasal Splints*; Jan. 25, 2007.
http://www.technologyforlife.com.au/ent/nasal.html; *Nasal Surgery and Accessories*; Jan. 25, 2007.
EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
European Search Report dated Sep. 27, 2011 re: EP10182961.
European Search Report dated Sep. 29, 2011 re: EP10182893.
International Preliminary Report on Patentability dated Aug. 25, 2006 from PCT/US05/25371.
International Preliminary Report on Patentability dated Oct. 4, 2007 from PCT/US06/002004.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report dated Jun. 3, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report dated Nov. 30, 2009 re: PCT/US2009/057203.
International Search Report dated Dec. 10, 2009 re: PCT/US2009/052236.
International Search Report dated Dec. 16, 2009 re: PCT/US2009/050800.
International Search Report dated Mar. 31, 2010 re: PCT/US2009/069143.
International Search Report dated Jul. 8, 2010 re: PCT/US2010/027837.
International Search Report dated Oct. 6, 2010 re: PCT/US2010/040548.

(56) References Cited

OTHER PUBLICATIONS

International Search Report dated Mar. 25, 2011 re: PCT/US2010/062161.
International Search Report dated Mar. 28, 2011 re: PCT/US2010/061850.
International Search Report dated Mar. 31, 2011 re: PCT/US2010/060898.
International Search Report dated Aug. 9, 2011 re: PCT/US2011/038751.
International Search Report dated May 18, 2012 re: PCT/US2011/052321.
Partial European Search Report dated Sep. 20, 2007 re: 07252018.
Partial European Search Report dated Mar. 25, 2008 re: 07252018.
Partial International Search Report dated Feb. 7, 2012 re: PCT/US2011/052321.
Supplemental European Search Report dated Jun. 2, 2008 re: EP05773189.
Supplemental European Search Report dated Jul. 1, 2009 re: EP06815285.
Supplemental European Search Report dated Jan. 29, 2010 from EP07836108.
Supplemental European Search Report dated Feb. 2, 2010 re: EP07836109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 re: 07777004.
Supplemental European Search Report dated Mar. 31, 2011 re: EP05798331.
Supplemental European Search Report dated Aug. 30, 2011 re: EP06800540.
Supplemental European Search Report dated Sep. 29, 2011 re: EP07750248.
U.S. Appl. No. 10/259,300 filed Sep. 30, 2002.
U.S. Appl. No. 10/259,630 filed Sep. 30, 2002.
U.S. Appl. No. 10/470,881 filed Feb. 4, 2004.
U.S. Appl. No. 10/829,917 filed Apr. 21, 2004.
U.S. Appl. No. 10/912,578 filed Aug. 4, 2004.
U.S. Appl. No. 10/944,270 filed Sep. 17, 2004.
U.S. Appl. No. 11/037,548 filed Jan. 18, 2005.
U.S. Appl. No. 11/116,118 filed Apr. 26, 2005.
U.S. Appl. No. 11/150,847 filed Jun. 10, 2005.
U.S. Appl. No. 11/193,020 filed Jul. 29, 2005.
U.S. Appl. No. 11/234,395 filed Sep. 23, 2005.
U.S. Appl. No. 11/347,147 filed Feb. 2, 2006.
U.S. Appl. No. 11/355,512 filed Feb. 16, 2006.
U.S. Appl. No. 11/436,892 filed May 17, 2006.
U.S. Appl. No. 11/436,897 filed May 17, 2006.
U.S. Appl. No. 11/438,090 filed May 18, 2006.
U.S. Appl. No. 11/522,497 filed Sep. 15, 2006.
U.S. Appl. No. 11/527,773 filed Sep. 25, 2006.
U.S. Appl. No. 11/544,009 filed Oct. 4, 2006.
U.S. Appl. No. 11/647,530 filed Dec. 27, 2006.
U.S. Appl. No. 11/648,159 filed Dec. 29, 2006.
U.S. Appl. No. 11/655,794 filed Jan. 18, 2007.
U.S. Appl. No. 11/725,151 filed Mar. 15, 2007.
U.S. Appl. No. 11/789,704 filed Apr. 24, 2007.
U.S. Appl. No. 11/789,705 filed Apr. 24, 2007.
U.S. Appl. No. 11/803,695 filed May 14, 2007.
U.S. Appl. No. 11/925,540 filed Oct. 26, 2007.
U.S. Appl. No. 11/926,326 filed Oct. 29, 2007.
U.S. Appl. No. 11/926,565 filed Oct. 29, 2007.
U.S. Appl. No. 11/928,097 filed Oct. 30, 2007.
U.S. Appl. No. 12/011,100 filed Jan. 23, 2008.
U.S. Appl. No. 12/100,361 filed Apr. 9, 2008.
U.S. Appl. No. 12/117,582 filed May 8, 2008.
U.S. Appl. No. 12/117,672 filed May 8, 2008.
U.S. Appl. No. 12/117,961 filed May 9, 2008.
U.S. Appl. No. 12/118,931 filed May 12, 2008.
U.S. Appl. No. 12/120,902 filed May 15, 2008.
U.S. Appl. No. 12/122,884 filed May 19, 2008.
U.S. Appl. No. 12/340,226 filed Dec. 19, 2008.
U.S. Appl. No. 12/341,602 filed Dec. 22, 2008.
U.S. Appl. No. 12/502,101 filed Jul. 13, 2009.
U.S. Appl. No. 60/844,874 filed Sep. 15, 2006.
U.S. Appl. No. 60/922,730 filed Apr. 9, 2007.
U.S. Appl. No. 61/052,413 filed May 12, 2008.
U.S. Appl. No. 61/084,949 filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.

(56) References Cited

OTHER PUBLICATIONS

USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.

\* cited by examiner

METHODS AND DEVICES FOR OSTIUM MEASUREMENTS

CROSS REFERENCES TO RELATED APPLICATIONS

This application is a divisional of United States patent application Ser. No. 11/799,459, filed Apr. 30, 2007, the entire disclosure of such application being expressly incorporated herein by reference.

FIELD OF THE INVENTION

The present invention relates generally to medical devices, systems and methods and more particularly to methods and devices for deter mining the size of an ostium.

BACKGROUND OF THE INVENTION

The skull contains a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing mucosal tissue and ultimately open into the nasal cavity. Normally, mucous produced by the mucosal tissue slowly drains out of each sinus through an opening known as an ostium. If the mucosal tissue of one of these passageways becomes in flamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States. Patients who suffer from sinusitis typically experience at least some of the following symptoms: headaches or facial pain; nasal congestion or post-nasal drainage; difficulty breathing through one or both nostrils; bad breath; and/or pain in the upper teeth.

One of the ways to treat sinusitis is by restoring the lost mucous flow. The initial therapy is typically drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery (FESS).

During FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even of ter multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those an atomical structures are part of the pathology.

New devices, systems and techniques are being developed for the treatment of sinusitis and other disorders of the ear, nose, throat and paranasal sinuses. For example, various catheters, guidewires and of her devices useable to perform minimally invasive, minimally traumatic ear, nose and throat surgery have been described in U.S. patent application Ser. No. 10/829,917 entitled "Devices, Systems and Methods for Diagnosing and Treating Sinusitis and Other Disorders of the Ears, Nose and/or Throat," now U.S. Pat. No. 9,654,997, issued Feb. 2, 2010, Ser. No. 10/912,578 entitled "Implantable Device and Methods for Delivering Drugs and Other Substances to Treat Sinusitis and Other Disorders," now U.S. Pat. No. 7,361,168, issued Apr. 22, 2008, Ser. No. 10/944,270 entitled "Apparatus and Methods for Dilating and Modifying Ostia of Paranasal Sinuses and Other Intranasal or Paranasal Structures" now U.S. Pub. No. 2006/0004323, published on Jan. 5, 2006, Ser. No. 11/037,548 entitled "Devices, Systems and Methods For Treating Disorders of the Ear, Nose and Throat", now U.S. Pat. No. 7,462,175, issued Dec. 9, 2008, and Ser. No. 11/116,118 entitled "Methods and Devices For Performing Procedures Within the Ear, Nose, Throat and Paranasal Sinuses," now U.S. Pat. No. 7,720,521, issued May 18, 2010. Each of these applications is hereby incorporated herein, in its entirety, by reference thereto. Many of these new devices, systems and techniques are use able in conjunction with endoscopic, radio graphic and/or electronic assistance to facilitate precise positioning and movement of catheters, guidewires and other devices within the ear, nose, throat and paranasal sinuses and to avoid undesirable trauma or damage to critical anatomical structures such as the eyes, facial nerves and brain.

For example, in one new procedure (referred to in this patent application as a "Flexible Transnasal Sinus Intervention" or FTSI), a dilatation catheter (e.g., a balloon catheter or other type of dilator) is advanced through the nose to a position within the ostium of a paranasal sinus or other location, without requiring removal or surgical alteration of other intranasal anatomical structures. The dilatation catheter is then used to dilate the ostium or other anatomical structures to facilitate natural drainage from the sinus cavity. In some cases, a tubular guide may be initially inserted through the nose and advanced to a position near the sinus ostium and a guidewire may then be advanced through the tubular guide and into the affected paranasal sinus. The dilatation catheter may then be advanced over the guidewire and through the tubular guide to a position where its dilator (e.g., balloon) is positioned within the sinus ostium. The dilator (e.g., balloon) is then expanded causing the ostium to dilate. In some cases, such dilatation of the ostium may fracture, move or remodel bony structures that surround or are adjacent to the ostium. Optionally, in some procedures, irrigation solution and/or therapeutic agents may be infused through a lumen of the dilatation catheter and/or other working devices (e.g., guidewires, catheters, cannula, tubes, dilators, balloons, sub stance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be advanced through the tubular guide and/or over the guidewire to deliver other therapy to the sinus or adjacent tissues during the same procedure in which the FTSI is carried out. It is to be understood that, in FTSI procedures, structures and passageways other than sinus ostia may be dilated using the tools described above, tissue may be resected or ablated, bone may be restructured, drugs or drug delivery systems may be deployed, etc., as described in the documents incorporated herein by reference. Thus, for the purposes of this application the term FTSI will be generally used to refer broadly to all of those procedures, not just dilation of sinus ostia.

In FTSI procedures that include positioning of a guidewire into a paranasal sinus, the placement of the guidewire is typically confirmed by visualizing the procedure under fluoroscopy or other x-ray visualization techniques. Currently, there is no simple and accurate method or apparatus to measure the size of an ostium, and in particular a sinus ostium. Surgeons often approximate the size of an ostium endoscopically by placing a sinus seeker with an atraumatic tip of known diameter near the ostium and estimating the size of the ostium. Unfortunately, this method lacks precision or accuracy in determining the size of an ostium.

Determining the ostium size of a nasal ostium prior to surgery enables the user of a balloon catheter to determine the appropriate amount of inflation needed to open the ostium to a size for sufficient drainage. Being able to accurately measure the ostium size after surgery is also useful in determining if the FTSI procedure was successful or if further treatment is needed. Thus there is a need for methods and devices that can accurately determine the size of the ostium pre-, post-, and during such procedures.

SUMMARY OF THE INVENTION

The present invention provides methods, devices and kits for measurement of sinus ostia. A method for determining the size of a sinus ostium according to at least one embodiment provided herein includes the steps of: positioning a sinus ostium measuring device internally into a patient, locating a target sinus ostium, positioning the sinus ostium measuring device adjacent to or in the target sinus ostium, and determining the diameter of the target sinus ostium with the sinus ostium measuring device.

In at least one embodiment, the sinus ostium measuring device is positioned adjacent to the target sinus ostium.

In at least one embodiment, the sinus ostium measuring device is positioned within the target sinus ostium.

In at least one embodiment, the distal end portion of the sinus ostium measuring device is initially inserted through a nostril of the patient and then advanced into a sinus.

In at least one embodiment, determining the diameter of the target sinus ostium measurement is observed when a portion of the distal end portion is located in the sinus of the patient.

In at least one embodiment, the distal end portion of the sinus ostium measuring device is advanced towards the opening of the sinus; and placement of the distal end portion of the sinus ostium measuring device adjacent to the opening of the sinus is confirmed by visualization techniques.

In at least one embodiment, the distal end portion of the sinus ostium measuring device is advanced through the opening of the sinus; and placement of the distal end portion of the sinus ostium measuring device in the sinus is confirmed by visualization techniques.

In at least one embodiment, the visualization techniques comprise endoscopic visualization.

In at least one embodiment, the visualization techniques in dude fluoroscopy.

A sinus ostium measuring device is provided, including: a flexible distal end portion; a relatively less flexible proximal end portion; and at least one marker to facilitate determination of the size of a target sinus ostium.

In at least one embodiment, the distal end portion of the sinus ostium measuring device has an outside diameter configured and dimensioned to pass through a sinus ostium of a sinus.

In at least one embodiment, the distal end portion of the device includes a bend, such that a proximal part of the distal end portion is substantially aligned with a longitudinal axis of the device, and a distal part of the distal end portion is angled with respect to the longitudinal axis.

In at least one embodiment, the sinus ostium measuring device comprises a distal end, and the distal end portion is rigid or malleable.

In at least one embodiment, the sinus ostium measuring device comprises a distal end, and the distal end portion comprises a ball tip at a distal end thereof.

In some embodiments, these sinus ostium measuring devices have lumens extending therethrough. In such embodiments having lumens, guidewires may be inserted or advanced through the lumen, thereby providing sinus ostium measuring/guidewire systems that are useable for placing guidewires into various anatomical structures (e.g., into a paranasal sinus). In some embodiments that have lumens, a slot opening may extend along all or a portion of the lumen to allow a guidewire or other elongate device to be extracted laterally from all or a portion of the lumen. Structurally, a sinus ostium measuring device of the present invention may comprise an elongate substantially rigid (e.g., straight, pre-shaped, bent, curved, malleable) shaft at the proximal end, and optionally having an atraumatic distal tip. Various curves may be formed or formable in the seeker shaft.

Further in accordance with the invention, there are provided sinus ostium measuring devices that are useable to locate or access structures within the ear, nose and throat.

Kits of sinus ostium measuring devices having different sizes adapted to measure a range of dimensions are provided.

These and other advantages and features of the invention will become apparent to those persons skilled in the art upon reading the details of the devices, methods and systems as more fully described below.

BRIEF DESCRIPTION OF THE DRAWINGS

FIG. 5b is a perspective view of the adjustment knob of the ostium measuring device of FIG. 5a.

FIG. 5c is a partial sectional view of the device of FIG. 5a.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the con text clearly dictates otherwise, between the upper and lower limits of that range is also specifically disclosed. Each smaller range between any stated value or intervening value in a stated range and any other stated or intervening value in that stated range is en compassed with in the invention. The upper and lower limits of these smaller ranges may independently be included or excluded in the range, and each range where either, neither or both limits are in eluded in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tube" includes a plurality of such tubes and reference to "the shaft" includes reference to one or more shafts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
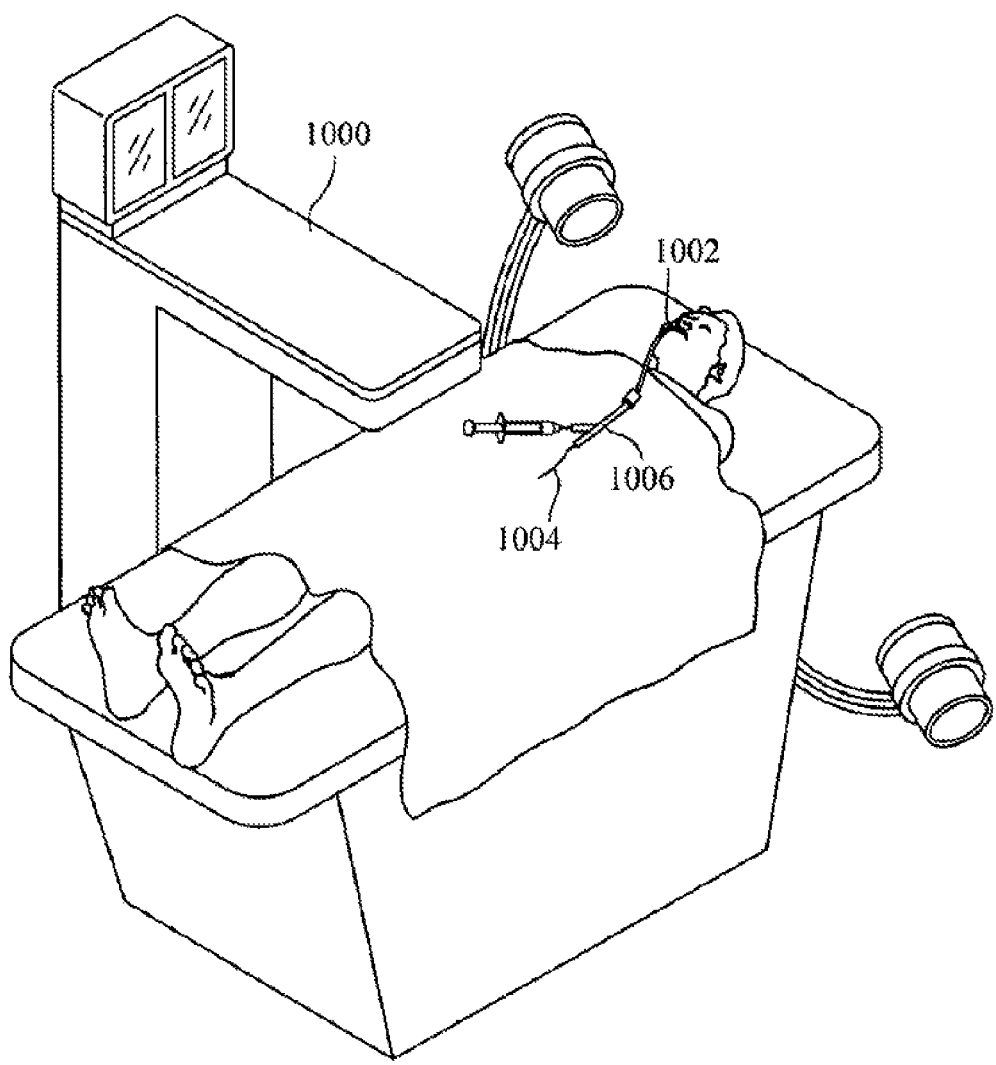
FIG. 1 is an illustration of a patient being treated by a system for catheter-based minimally invasive sinus surgery according to prior art techniques.

Turning now to FIG. 1, an illustration of a patient being treated by a system for catheter-based minimally invasive sinus surgery according to prior art techniques is shown. A C-arm fluoroscope 1000 that is useable to visualize a first introducing device 1002 (e.g., a sinus guide, guide catheter or guide tube), a second introducing device 1004 (e.g., a guidewire or elongated probe) and a working device 1006 (e.g., a balloon catheter, other dilatation catheter, debrider, cutter, etc.). The sinus guide, guide catheter or guide tube 1002 may be introduced under direct visualization, visualization provided by fluoroscope 1000 and/or from endoscopic visualization, to place the distal end of catheter or tube 1002 at a location approaching an ostium of a sinus to be treated.

Next guidewire or elongated probe 1004 is inserted through catheter or tube 1002 and distally advanced to extend the distal end of guidewire or elongated probe through the ostium to be treated and into the sinus that the ostium opens to. Proper placement often involves advancement and retraction of the distal end of guidewire or elongated probe, under fluoroscopic visualization, until it has been visually confirmed that the distal end of the guidewire or elongated probe is located where the surgeon believes the appropriate sinus to be located, relative to the other features of the patient's head that are visualized under fluoroscopy.

Once guidewire or elongated probe 1004 has been properly placed, working device 1006 is next passed over the guidewire or elongated probe 1004, under visualization via fluoroscope 1000 and/or an endoscope (not shown) that has been inserted adjacent catheter or tube 1002, to place the working end of working device 1006 in the target location where a surgical procedure is to be performed. Typically, the guidewire or elongated probe 1004 remains in place during the procedure. Under the same type(s) of visualization, the working (distal) end of working device 1006 is then actuated to perform the desired surgical procedure. In the case of a dilation catheter, the balloon at the distal end portion of catheter 1006 is expanded once it has been located across the ostium. This expansion acts to open the ostium to allow proper mucus flow. After performance of the desired surgical procedure, the working device 1006 is deactivated and withdrawn from the patient, after which the remaining devices are withdrawn to complete the procedure.

By using the devices and methods described herein, accurate measurement of the sinus ostia is important for pre-operative and intra-operative planning. For example, a surgeon may wish to know the size of the ostium prior to choosing a balloon for dilation. Also, it is useful to document the size of the dilated ostium, both immediately after the dilation and weeks or months post operatively to determine the overall success of the surgery.

It is to be appreciated that the devices and methods of the present invention relate to the measuring, accessing and dilatation or modification of sinus ostia or other passageways within the ear, nose and throat. These devices and methods may be used alone or may be used in conjunction with other surgical or non-surgical treatments, including but not limited to the delivery or implantation of devices and drugs or other substances as described in co-pending U.S. patent application Ser. No. 10/912,578, now U.S. Pat. No. 7,361, 168, issued Apr. 22, 2008.

Figure 2A:
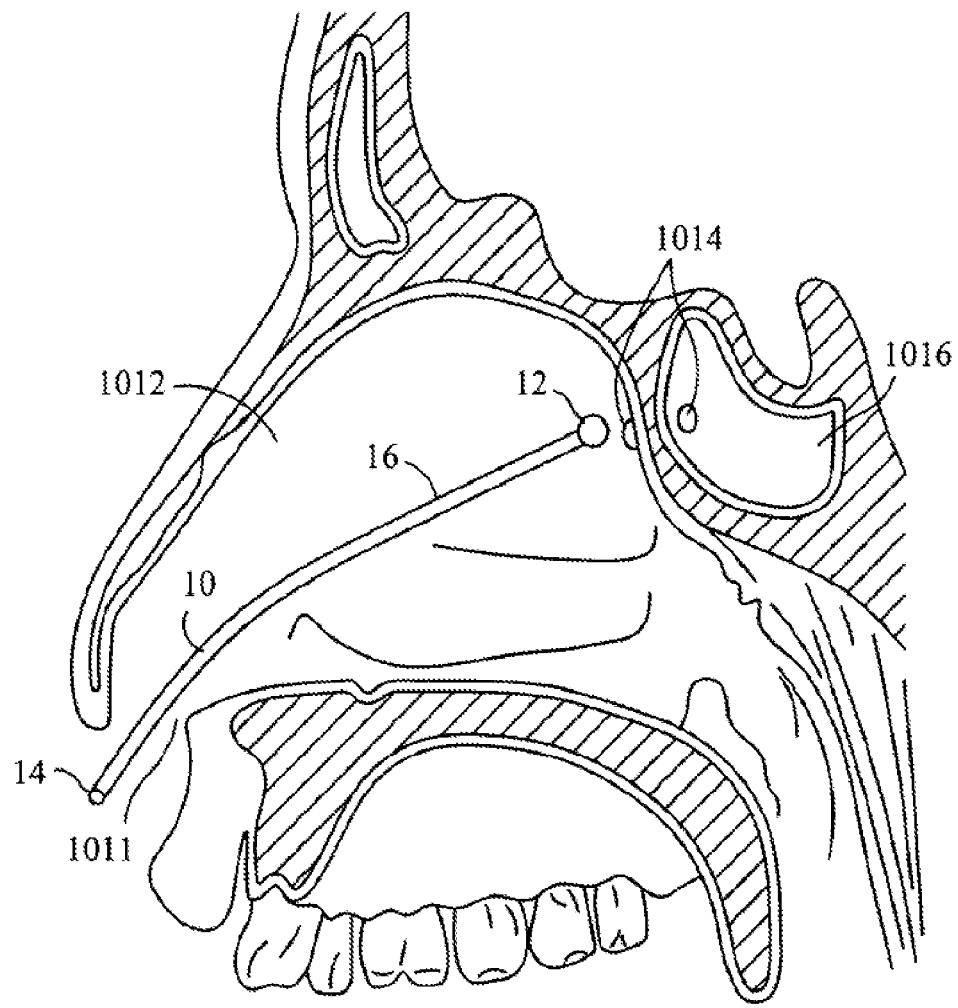
FIGS. 2a is an illustration of a partial sagittal sectional view through a human head showing one embodiment of a sinus ostium measuring device in accordance to the invention.

FIG. 2a is an illustration of a partial sagittal sectional view through a human head showing one embodiment of a ostium measuring device 10 within a paranasal sinus in accordance with the invention. Ostium measuring device 10 comprises a distal end 12 and proximal end 14, where the distal end has a spherical or ball shape configured to measure a sinus ostium. Distal and proximal ends 12, 14 are joined or coupled to an elongated shaft or body 16. The proximal end 14 of ostium measuring device 10 and the adjacent portion of shaft 16 may be straight or curvilinear, rigid, semi-rigid, resilient or malleable, or it may in corporate one or more preformed curves or bends to allow better access of the distal end 12 to an ostium. In embodiments where the shaft 16 and/or proximal end 14 of ostium measuring device 10 is curved or bent, the deflection angle of the curve or bend may be in the range of up to about 135 degrees. The curvature of the device 10 may range, for example, from about zero to about 120 degrees. Several examples of embodiments include bends of about zero degrees, about 30 degrees, about 70 degrees, about 90 degrees and about 110 degrees, respectively.

In embodiments wherein the proximal end 14, distal end 12 and/or shaft 16 are malleable or resilient or contain portions which are malleable or resilient, such portions may be made from materials such as metallic tubes, rods (e.g. rods embedded in a shaft or wire. Suitable biocompatible material(s) that can be used for construction of an ostium measuring device in dude but are not limited to metals e.g. malleable stainless steel, fully annealed stainless steel, copper, aluminum, titanium, nickel-titanium alloy (e.g., Nitinol), etc.; and polymeric materials such as polyether block am ides (e.g., Pebax), polyether ether ketone (PEEK), Nylon, polyethylene, polyurethane, etc., which may be in the form of glass or carbon-reinforced composites.

The proximal end 14 in many embodiments may be configured to couple to a handpiece (not shown) or be inserted into a guide catheter (not shown) to increase stability and/or facilitate the placement of the ostium measuring device 10 when inserted into an opening in a patient, such as a nostril or ear. The proximal end 14 may comprise portions which are rigid while other sections of the proximal end 14 may be resilient or malleable and made of materials mentioned above. The flexible nature of ostium measuring device 10 allows for passage and tactile feedback to the user through tortuous anatomy.

Figure 2B:
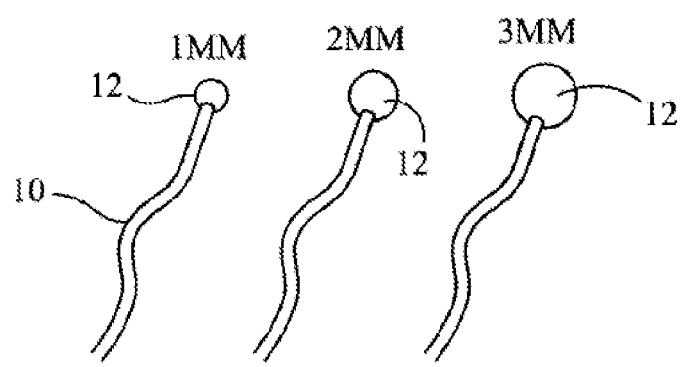
FIG. 2b is a perspective view of various sized distal portions of sinus ostium measuring devices in accordance with the invention.

The distal end 12 of the ostium measuring device 10 may vary in size as shown in FIG. 2b. The diameter of the distal end 12 may be in the range from about 0.5 mm to about 6.0 mm, more preferably about 1 mm to about 3 mm, and a kit of devices 10 may be provided with diameters having incremental differences of about 0.5 mm, for example, or other incremental variations, e.g., in the range of about 0.25 mm to about 1.0 mm, for example. Having a range of sized ostium measuring devices 10, allows the user to identify which sized distal end best fits in or near the target ostium, better enabling the size of the ostium to be determined. The distal end 12 may be made of materials to aid in visual navigation to locate the target ostium within the patient. Such materials may include but are not limited to at least one radio-opaque marker (e.g., comprising platinum, tungsten, stainless steel, or the like), electromagnetic, piezoelectric or magnetic materials, depending on the visual navigational technique being utilized for ostium measurement. Distal end 12 may be detachable and interchangeable to allow use of differently sized or shaped ends 12. Further optionally, coatings such as reflective coatings and/or polarized coatings may be applied to improve visibility thereof view endoscopic visualization. Colored coating may be applied to proved better contrast with surrounding tissues when the distal end is in situ and being viewed via endoscopic visualization, for example.

Some embodiments of the invention may utilize fluoroscopy or other x-ray techniques in combination with, or in lieu of endoscopic visualization, to navigate the ostium measuring device 10 to the target ostium and also to determine the diameter of the target ostium by a fluoroscopic image. The measuring device 10 may comprise radio-opaque markings on a portion of the distal end 12 which is descriptive of the diameter of the at particular ostium measuring device 10 being used. Such markings may include but are not limited to lines, stripes or solid marked spherical ends correlating to a certain sized distal end 12. The distal end 12 may also comprise indicia with in the radio-opaque marking to aid the user in identifying which size measuring device is being utilized at that particular moment.

FIG. 2a also depicts various steps in a method of measuring an ostium with an ostium measuring device 10 in accordance with the invention. The method comprises, in general terms, introducing an ostium measuring device 10 through a nostril 1011 and through a nasal cavity 1012 to a location close to a target ostium such as, for example, ostium 1014 of a sphenoid sinus 1016. The method further comprises placing the distal end 12 of ostium measuring device 10 into the target ostium 1014. If the distal end 12 moves easily through the ostium 1014, an ostium measuring device 10 comprising a larger distal end 12 is utilized until a compatible fit of the distal end 12 of the ostium measuring device 10 with the target ostium 1014 has been determined by the user. After the ostium 1014 has been measured, ostium measuring device 10 is withdrawn and removed. It will be appreciated that the present invention may also be used to measure any sinus ostium or other man-made or naturally occurring anatomical opening or passageway within the nose, paranasal sinuses, nasopharynx or adjacent areas.

FIG. 2b is an illustration of three ostium measuring devices 10 with spherical distal ends 12 of varying sizes. The size of the spherical distal end 12 of the ostium measuring device of the embodiments shown in FIGS. 2a and 2b, range, for example, from about 0.5 mm to about 6 mm in diameter, and more preferably from about 1 mm to about 5 mm. The distal end 12 may be oblong or oval in shape in order to better fit certain shaped target ostia such as ostia of the frontal, sphenoid and/or maxillary sinuses, for example. In these embodiments, the distal end 12 of the measuring device 10 will have two diameters, i.e. the length and width distances of the oblate or oval shape, allowing two ostium measurements to be taken using the same distal end 12.

The various sized ostium measuring devices 10 may be provided to the user in the form of a kit. The ostium measuring kit in certain embodiments comprises at least two ostium measuring devices 10, each ostium measuring device 10 comprising a distal 12 and an proximal end 14, the distal end 12 varying in diameter for each ostium measuring device within the kit and the proximal end identifying the size of the distal end. The diameter of the distal ends may vary in increments of about 0.5 mm to about 1 mm. The kit may be used pre-, post- and/or during surgery to determine the size of the target ostium. In some embodiments, each measuring device within the kit comprises a unique radio-opaque marking which distinguishes it from the other ostium measuring devices 10 within the kit. The radio-opaque markings allow the user to navigate the measuring devices to the target ostium and determine the size or diameter of the ostium by knowing the diameter of the ostium measuring device which provides the best fit with the target ostium. In another embodiment, each measuring device within the kit comprises a unique colored coating or marking which distinguishes it from the other ostium measuring devices 10 within the kit.

Another embodiment of the kit may comprise a single ostium measuring device with at least three detachable and interchangeable distal ends 12 of varying size or diameter. The distal ends 12 may be releasibly fastened to the device 10 by interfitting threading, snap fitting, tensional engagement, friction fit or other coupling means.

Figure 3A:
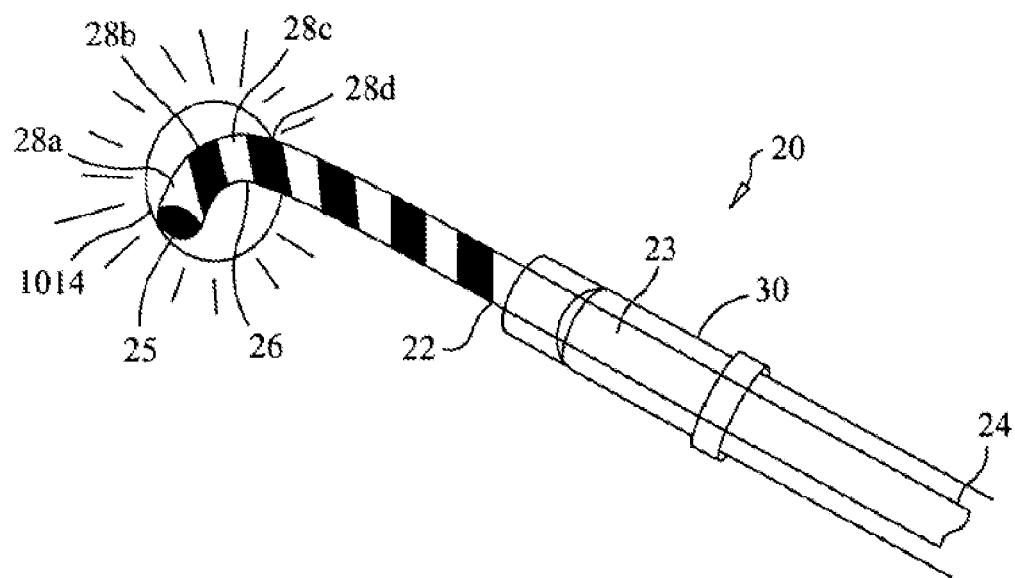
FIG. 3a is a perspective view of one embodiment of a sinus ostium measuring device comprising a flexible measuring strip in accordance with the invention.
Figure 3B:
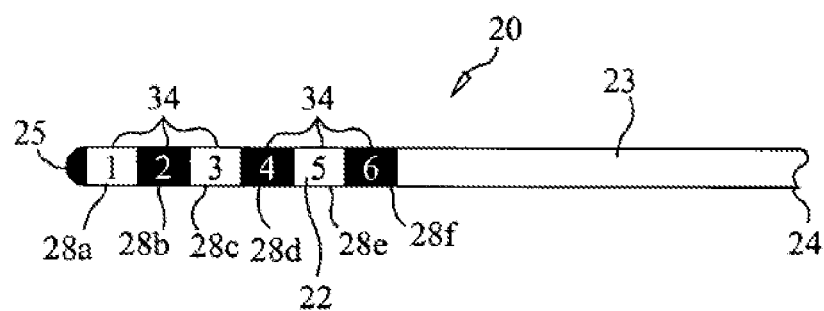
FIG. 3b is a perspective view of the flexible measuring strip of the device in FIG. 3a, comprising indicia in accordance with the invention.

Referring to FIGS. 3a and 3b, there is shown an other embodiment of an ostium measuring device 20 in accordance with the invention. The ostium measuring device 20 shown in FIG. 3a, comprises a distal end portion 22, a shaft or body 23, and proximal end portion 24. The distal end portion 22 is configured to facilitate measurement of the size of a target ostium. Both the distal and proximal end portions, 22 and 24 respectively, as well as shaft 23, have a substantially flattened or ribbon shape in the embodiment shown in FIGS. 3a and 3b. The distal end portion 22 further comprises an atraumatic tip 25 so as not to damage patient tissue while locating the target ostium. The distal end portion 22 may further comprise at least one flexible or malleable portion 26 to aid in the maneuvering of the measuring device 20 within a patient. In certain embodiments, the distal end portion 22 is configured to enable a curve 26 to be set in the distal end portion to aid in the measuring of surfaces normal to the long axis of the measuring strip. The embodiment shown in FIGS. 3a and 3b comprises a flexible ribbon 20 that is deliverable to a sinus ostium by use of a guide catheter 30, in a manner as illustrated in FIG. 3a. The ribbon material is such that a preset curve can be applied to the distal tip portion. The material may comprise, but is not limited to one or more of the following: malleable stainless steel, Nitinol, spring tempered stainless steel, nylon, polyimide, Pebax, PEEK. The atraumatic tip 25 of the ribbon 20 may have rounded, beveled or chamfered edges.

In many embodiments, the distal end portion 22 of ostium measuring device 20 further comprises stripes or markings 28a, 28b, 28c, 28d, etc. which are visible by endoscopy and/or fluoroscopy or other x-ray imaging techniques to aid in measuring the target ostium. Other indicators may be used alternatively to stripes, such as dots, dotted lines, or other markers. The markings 28a, 28b,28c,28d, 283, 28f, etc. may be of alternating contrasting stripes of known height and width to allow the user to endoscopically view and count the stripes and thereby determine the diameter of the target ostium. Note, that although six such stripes are shown in FIG. 3b and ten such stripes are shown in FIG. 3a, the present invention is not limited to these numbers of stripes, as the total number of stripes may vary, depending upon the height and width of the stripes and upon the particular application for which that particular device is designed to be used. Additionally, or alternatively, the markings 28a, 28b, 28c, 28d, etc. may be of alternating radio-opaque and radio-transparent stripes of known height and width to allow the user to count the stripes and determine the diameter of the target ostium. The height and width size of the stripes 28a, 28b, 28c, 28d may vary depending on the type of ostium that the device is designed to measure. Generally, the alternating stripes 28a, 28b, 28c, 28d are of equal height and are evenly spaced, each by about 1 mm in width, but in some embodiments the incremental changes in width can be smaller, e.g. about 0.5 mm in width. In certain embodiments the height of each stripe may vary incrementally, such that stripes 28a, 28b, 28c, 28d, etc., are 0.5 mm, 1.0 mm, 1.5 mm, 2.0 mm, etc., in width, in ascending or descending order, i.e., an increment of change in height of 0.5 mm. In other embodiments, the increment of change in height between each stripe may be smaller or greater than 0.5 mm, e.g., 0.25 mm, 0.3 mm, 0.6 mm or some other incremental value. In other embodiments each stripe 28a, 28b, 28c, 28d is of the same height.

The malleable portions as well as semi-rigid portions of the ostium measuring device 20 may be made from materials such as metallic or polymeric ribbon. Suitable biocompatible material(s) that can be used for construction of an ostium measuring device 20 include but are not limited to metals e.g. malleable stainless steel, fully annealed stainless steel, copper, aluminum, titanium, nickel-titanium alloy (e.g., Nitinol), etc.; polymers e.g. Pebax, PEEK, Nylon, polyethylene, polyimide, etc, as described for the embodiment of FIG. 2a and FIG. 2b above.

Proximal end portion 24 and shaft 23 of the ostium measuring device 20 can be positioned within a guide catheter handpiece 30. The guide catheter 30 comprises a threaded luer (not shown) which is configured to releasibly hold the shaft 23 and proximal end portion 24 in place during ostium measurement. The luer may be loosened to allow extension or retraction of shaft 23 from guide catheter 30, and then tightened when distal end portion 22 is in a desired position. The guide catheter apparatus and the methods of positioning a tool such as the ostium measuring device into a guide catheter apparatus are described in U.S. patent application Ser. No. 11/193,020 entitled "Methods and apparatus for treating disorders of the ear, nose and throat", now U.S. Pub. No. 2006/0063973, published Mar. 23, 2006, Ser. No. 11/150,847 entitled "Devices, Systems and Methods Useable for treating Sinusitis," now U.S. Pub. No. 2006/0284428, published Dec. 21, 2006, and incorporated herein.

In some embodiments, the distal end portion 22 of the measuring device 20 will further comprise indicia as illustrated in FIG. 3b. FIG. 3b shows a distal end portion 22 with alternating stripes of contrasting colors, optically transparent and opaque material, and/or radio-opaque and radio-transparent regions 28a, 28b, 28c, 28d, 28e and 28f, each region having a unique indicia, number or other alphanumeric symbol 34 which represents a certain distance from the atraumatic tip 25 of distal end portion 22. The indicia 34 are readable by endoscopic and/or fluoroscopic or x-ray techniques. When the indicia 34 are numerical, the number may represent the distance in millimeters each stripe 28a 28b etc. is from the tip of the distal end of the measuring device. Having indicia 34 on the stripes 28 34 is beneficial when it is necessary to place a large amount of curvature on the distal end portion 22 when making an ostium measurement. By adding numbers 34 to the striped portions 28a, 28b, 28c, 28d, etc., of the distal end portion 22 which correlate to a predetermined distance of the measuring device 20, the user is able to quickly determine the diameter of an ostium. Alternatively, the indicia may directly identify the values of the widths of the stripes that they occur on.

Figure 4A:
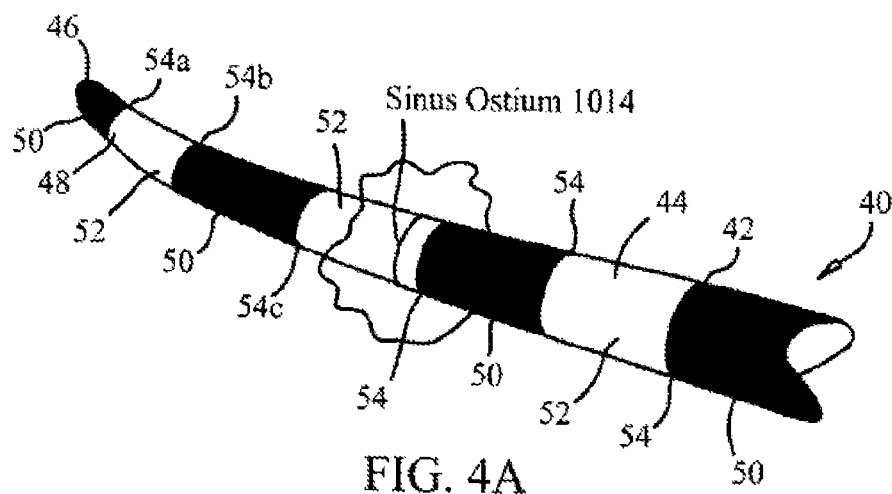
FIGS. 4a-c are perspective views of embodiments of a sinus ostium measuring device comprising a tapered mandrel in accordance with the invention.
Figure 4B:
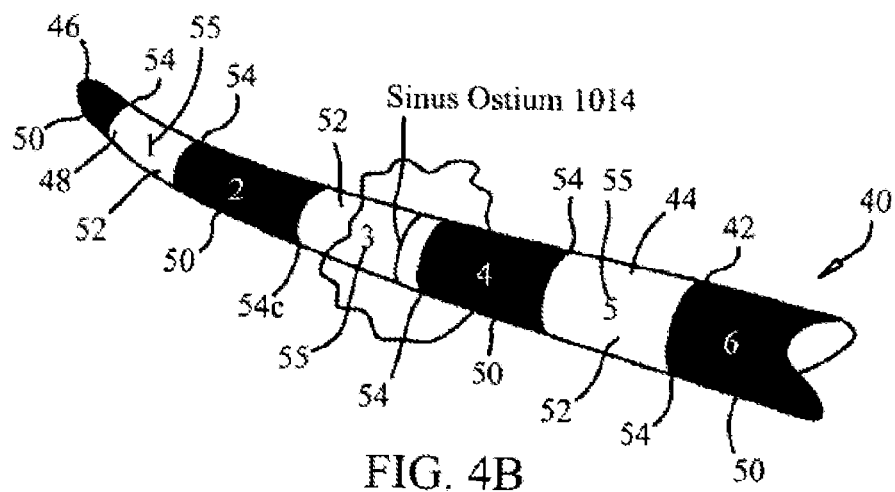
Figure 4C:
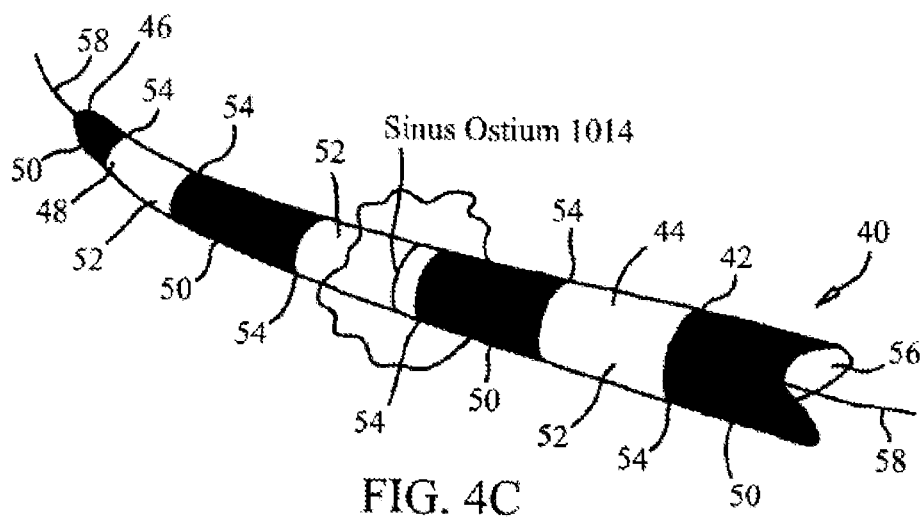

FIGS. 4a-c illustrate further embodiments of a distal portion of an ostium measuring device 40 shown placed within a target ostium 1014 in accordance with the invention. The ostium measuring device 40 shown in FIGS. 4*a-c* comprises a distal end portion 42 as well as a shaft and a proximal end portion (not shown). The distal end portion 42 has a tapered mandrel portion 44. The measuring device 40 further comprises an atraumatic tip 46 at the smaller end 48 of the tapered mandrel portion 44. The diameter of the atraumatic tip 46 is small enough to fit into the target ostium, smaller end portion 48 first, allowing the tapered mandrel 44 to move through the ostium until the outer circumference of the distal end portion 42 of the measuring device 40 fits snuggly in the ostium 1014.

The tapered mandrel portion 44 may further comprise visually contrasting and/or radio-opaque 50 and alternating (in contrast, or radio-transparent) markings 52 to help navigate the ostium measuring device 40 by visual techniques such as endoscopy, fluoroscopy and other x-ray techniques. Adjacent markings or stripes 50, 52 are separated by a boundary or interface 54 of known or pre-determined diameter. The markings 50, 52 allow the user to determine the size of the ostium 1014 by counting the number of stripes 50, 52 and portions thereof on the measuring device 40 which are able to move through the ostium 1014 as shown in FIG. 4*a*. For example, the interface 54*a* in FIG. 4*a* between alternating stripes 50, 52 may represent a predetermined outer diameter of 1 mm at that particular point on the mandrel portion 44 of the measuring device 40. Interfaces 54*b*, 54*c* respectively indicate in creases in the outer diameter of the device 40 in similar increments of 1 mm (i.e. 2 mm, 3 mm etc.) or by 0.5 mm increments (i.e. 1.5 mm, 20 mm), or other incremental increases in diameter. Thus by counting the stripes 50, 52 the user can determine at what point the ostium 1014 has a similar diameter and circumference as the outer diameter of the ostium measuring device 40. The interfaces 54 may represent smaller or larger incremental changes in the outer diameters of the measuring device depending on the ostium to be measured.

FIG. 4*b* shows one embodiment of a measuring device 40 which further comprises indicia or alphanumeric symbols 55 on the stripes 50, 52 of the tapered mandrel portion 44. The indicia 55 may indicate the outer diameter of the ostium measuring device at that particular position (or the diameter at an adjacent boundary 54) along the longitudinal axis of the distal end portion 42 of the measuring device 40, thus allowing the user to identify the diameter of the ostium in relation to a "close fit" position with the measuring device 40. In some embodiments the numerical indicia are in increments of 0.5 mm (i.e. 0.5, 1.0 mm, 1.5 mm etc.) indicating the diameter of the tapered mandrel portion 44 at that particular point on the length of the device as shown in FIG. 4*b*. Other embodiments may involve having indicia 55 which indicates the circumference of the measuring device at specific positions, such as the interface or boundaries 54 between adjacent stripes 50, 52, allowing the circumference of the target ostium 1014 to be determined easily by the user. It is noted that in all the cases described herein, the placement of the measuring device can be aided by the use of a guide catheter.

In some embodiments, the ostium measuring devices of the present invention may comprise a lumen or channel 56 extending therethrough as illustrated in FIG. 4*c*. The ostium measuring device 40 shown in FIG. 4*c* further comprises an opening (not shown) at the atraumatic tip 46, which communicates with lumen 56 and is large enough for a guidewire 58 to be inserted in the lumen 56 of the device and through the opening in the atraumatic tip 46. This allows the ostium measuring device 40 to be conveniently inserted in the target ostium 1014 during a surgical procedure to check or measure the size of the ostium to determine if the ostium needs to be enlarged or is of an adequate size to permit sufficient drainage from the sinus associated with the target ostium. Additionally or alternatively, the measuring device 40 allows a guidewire to be steered to the target ostium. That is, measuring device 40, when provide with a lumen to insert a guidewire therethrough, can function like a guide catheter. The distal end of measuring device can be placed just outside of a target sinus ostium and the guidewire can be pushed through the measuring device, through the target sinus ostium and into the sinus. Alternatively, the distal end of the measuring device can be place in the sinus ostium and then the guidewire can be fed into the sinus, through the measuring device. In this regard, some embodiments further comprise a slot (not shown in FIG. 4*c*) down a portion or all of the lumen to allow a guidewire 58 or other elongate device to be extracted laterally from all or a portion of the lumen 58 of the ostium measuring device 40.

Figure 5A:
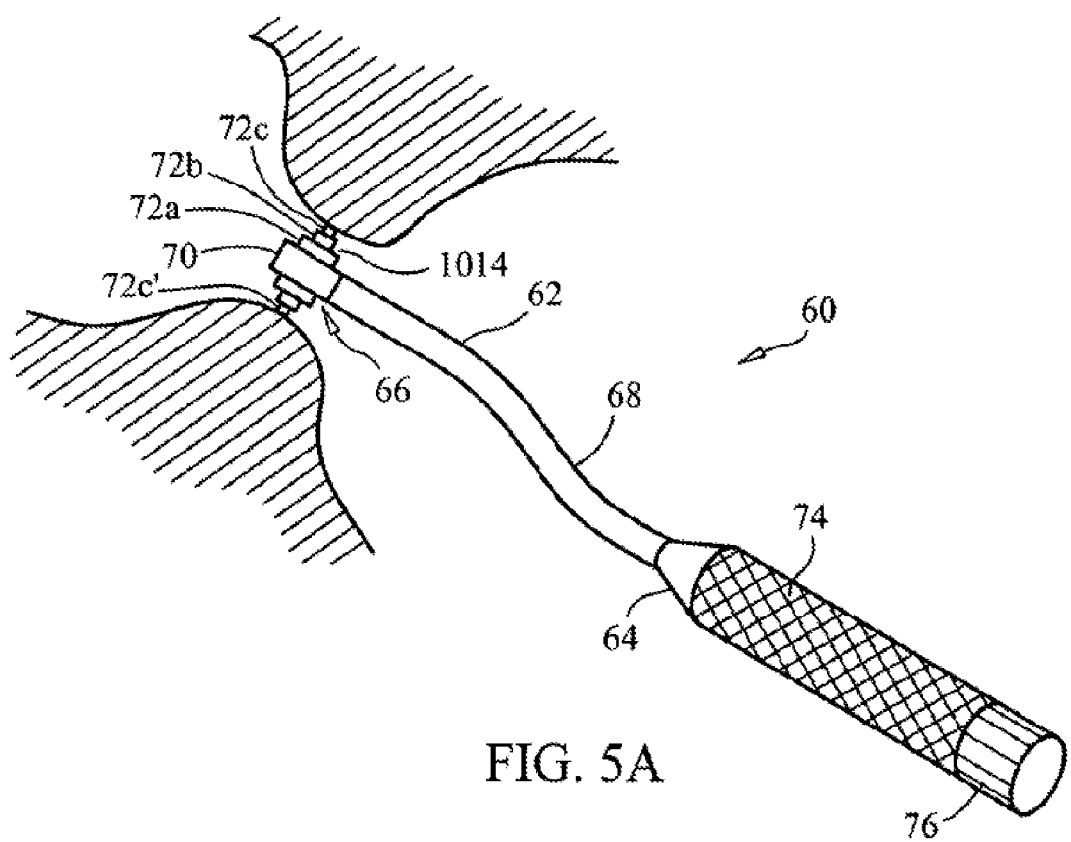
FIG. 5a is perspective view of an ostium measuring device comprising telescoping measurement portion in accordance with the invention.
Figure 5B:
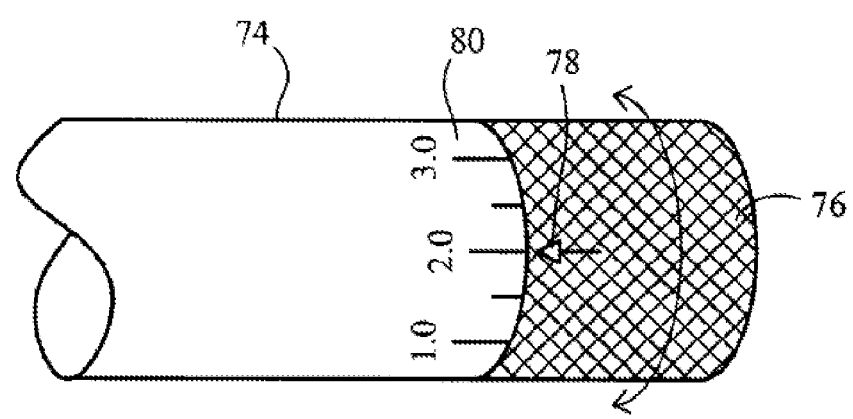
Figure 5C:
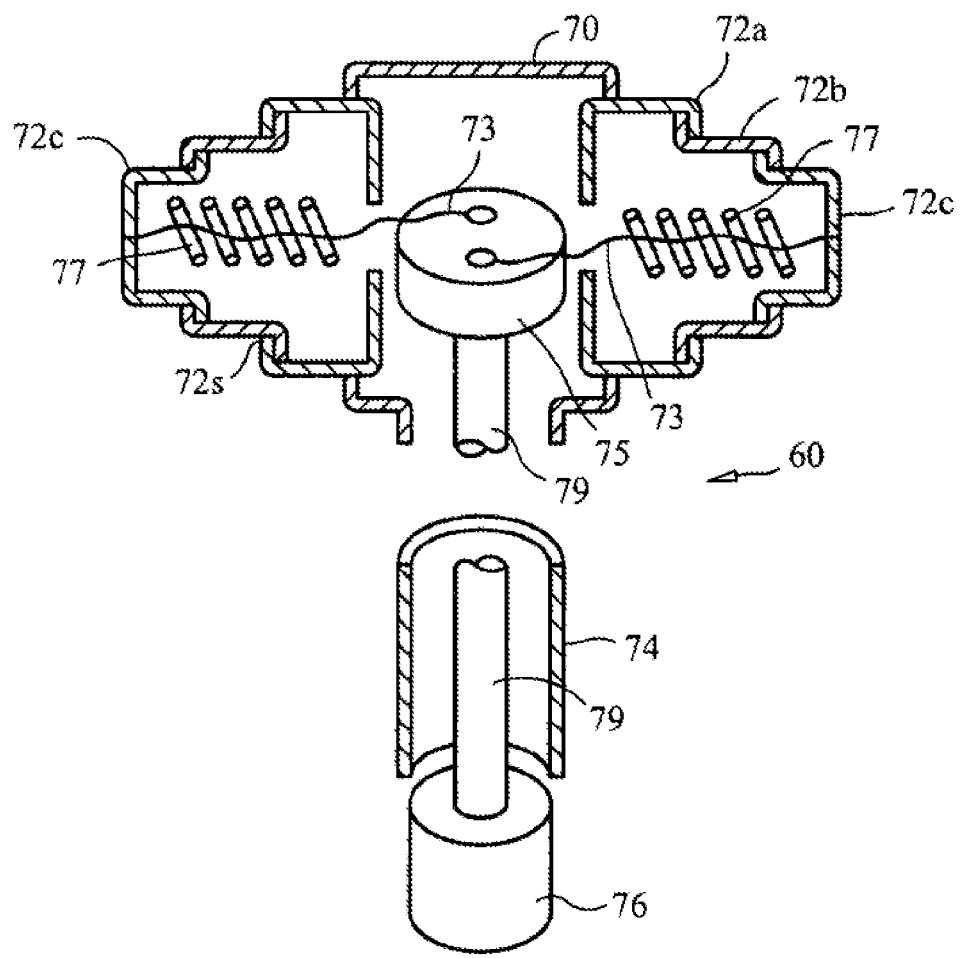

Referring now to FIGS. 5*a*-5*c*, illustrations of another embodiment of an ostium measuring device 60 in accordance with the invention are shown. The ostium measuring device 60 shown in FIGS. 5*a*-5*c* comprises a distal end portion 62 and a proximal end portion 64. The distal end portion 62 has a telescoping or extensible measurement portion 66 for measuring the size of a target ostium 1014 and a flexible or malleable shaft portion 68 interconnecting the proximal end portion 64 and distal end portion 62. The telescoping measurement portion 66 comprises a central housing 70 and a plurality of interfitting extension elements or features 72*a*, 72*b*, 72*c* with incrementally decreasing profiles, so that the features are nestable within one another. That is, the extension elements 72 have interior spaces configured to receive the next adjacent extension element therein, except for the outermost elements 72*c*. This allows the extension elements to collapse or retract within one another towards the central housing 70 of the telescoping measurement portion of the device 60, and, alternately, to extend outward from the collapsed configuration to an extended configuration from the housing 70. Extension can be continuous, so that continuously varying diametrical distances can be achieved by the extending elements. Elements 72*a*, 72*b*, 72*c* are hollow and are configured such that, in a retracted position, feature 72*b* fits within feature 72*a*, and feature 72*c* fits with in feature 72*b*. This arrangement is not limited to three features 72 per side, as more of fewer telescoping features 72 could be provided on each side.

FIG. 5*c* shows a partial sectional view of device 60 to illustrate the functionality thereof. In the embodiment of FIG. 5*c*, extension elements 72 are biased toward the fully extended configuration shown in FIG. 5*c*, by biasing elements 77. As shown, biasing elements 77 are coiled compression springs that extend between the base of a largest extension element 72*a* and a smallest extension element 72*c*. However, alternative biasing elements may be employed, such as leaf springs, or other biasing elements. FIG. 5*c* also illustrates shoulders 72*s*, or other abutment features provided on extension elements that prevent the extension elements from over-extending and thus separating from an adjacent extension element. The proximal end portion 64 further comprises a handle or handpiece 74 with an adjustment knob 76 configured to ad just the configuration/positions of extension elements 72 of the telescoping measurement portion 66 by mechanical control through the longitudinal axis of the handle 74, flexible shaft 68 and central housing 70. That is, shaft 79 is connected to control knob 76 at a proximal end of the shaft, and is connected to rotor 75 at a distal end of the shaft. Wires or tethers 73 interconnect the outermost extension elements 72c with rotor 73 on opposite sides of the rotor from the center of the rotor. In this way, when an operator rotates actuator 76 while maintaining handle 74 fixed, this rotates shaft 79 and rotor 75 which draws tethers 73 toward the central housing 70, thereby retracting extension elements 72 toward the central housing. Reverse rotation of the actuator 76 removes tension from tethers 73, allowing biasing elements 77 to drive extension elements outwardly from the central housing 70. Thus, rotatable adjustment knob 76 is mechanically coupled to extension elements 72a, 72b, 72c, such that rotation of knob 76 in one direction results in extension of extension elements 72a, 72b, 72c from housing 70, while rotation of knob 76 in the opposite direction results in collapse or retraction of extension elements 72a, 72b, 72c into or towards housing 70.

Figure 5D:
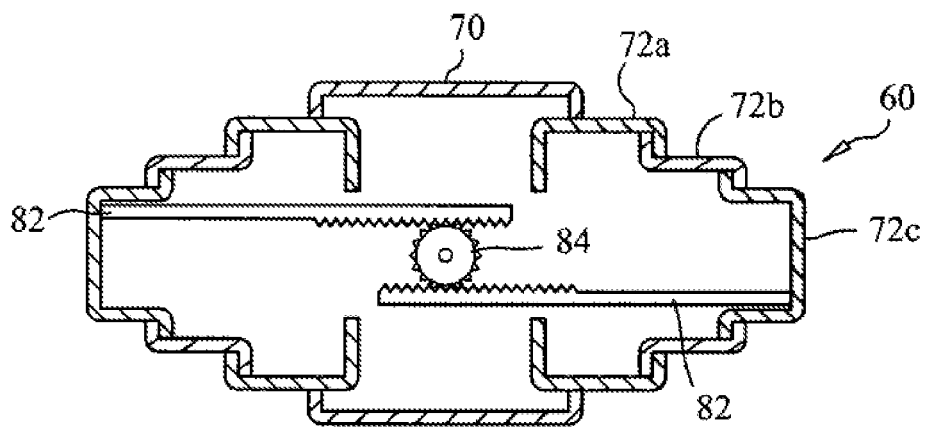
FIG. 5d is a sectional view of a device (viewed from the distal end of the device) having an alternative mechanism for controlling extension and retraction.

FIG. 5d is a sectional view of a device 60 (viewed from the distal end of the device) having an alternative mechanism for controlling extension and retraction. In this embodiment, racks 82 are provided to connect with the outermost extension elements 72c, at one end of each respective rack 82. The opposite end portions of racks 82 are meshed with pinion 84 that is mounted on shaft 79. Thus, rotation of actuator 76 in one direction drives racks 82, via pinion 84 in directions away from central housing 70, thereby extending elements 72, and rotation of actuator 76 in the opposite direction drives racks 82, via pinion 84, in directions toward the central housing 70, thereby retracting elements 72.

Extension elements 72a, 72b, 72c may be tapered in shape such that the outside diameter of the inner or base portion of element 72b is greater than the inside diameter of the outer or top portion of underlying element 72a, so that when fully extended, the base portion of element 72b does not extend past or exit the top portion of element 72a. Similarly, the outside diameter of the inner or base portion of element 72c may be greater than the in side diameter of the outer or top portion of underlying element 72b, so that when fully extended, the base portion of element 72c is prevented from extending past or exiting the top portion of element 72c.

Ostium measuring device 60 comprises two groups of individual extension elements 72a, 72b, 72c, with the outermost extension elements 72c having the smallest dimensions (e.g., diameter), and having the largest distance from the central housing 70 when the two groups of extension elements 72a, 72b, 72c are fully extended from housing 70. The distal end portion 62 of the ostium measuring device 60 has a size or diameter, when the individual extension elements are contracted, that is smaller than the size or diameter of the target ostium 1014, allowing the distal end portion 62 to be placed within the target ostium. Once the distal end portion 62 is positioned in the target ostium, the user rotates the adjustment knob 76 to extend the extension elements 72a, 72b, 72c until the outermost extension elements 72c, 72c' contact the wall of the ostium 1014. In at least one embodiment, elements/features 72 are extended until they can no longer be extended, as the force of extension is insufficient to dilate the ostium, so the most extended position of the elements 72 reliably measures the diameter of the ostium.

The knob 76 may further include a marking or arrow 78 adjacent to the handpiece 74, to allow the user to correlate the position of the knob 76 to the handpiece 74 while turning the knob 76 to change the distance between the outmost extending features 72c, 72c'. The handpiece 74 may further include indicia 80 adjacent to the adjustment knob 76 such that when the arrow 78 on the knob 76 points to or is adjacent to a particular number or indicia 80, (i.e. 2 mm) the indicia corresponds to the distance between the out most extending features 72c, 72c', thus giving the diameter of the target ostium 1014. For example, FIG. 5b shows indicia of 1.0, 2.0 and 3.0 on the handpiece, relating to a distance between the outermost surfaces of the outermost extension elements 72c, 72c' of 1 mm, 2 mm and 3 mm, respectively.

The indicia 80 on the handpiece 74 may vary depending on the size of the target ostium 1014 to be measured and/or the configuration of the features 72. Some indicia 80 may be in increments of about 0.5 mm, for example, while other devices may have the indicia in increments of about 1.0 mm, or 0.25 mm, or other increment, for example. The number of indicia 80 on the handpiece 74 may also vary depending on the range of variable distance the outermost extending features 72c, 72c' can achieve. For example if the largest distance between the outermost extending features is 5 mm, their may be 6 numerical indicia 80 on the handpiece 74, e.g. 0.0, 1.0, 2.0, 3.0, 4.0 and 5.0 mm, as well as, optionally, other indicia or gradations therebetween.

The distal end portion 62 may further comprise radio-opaque markings (not shown) to allow visual navigation to locate the target ostium 1014 with the ostium measuring device 60 by fluoroscopic or other x-ray techniques. The radio-opaque markings may be on the central housing 70 or at least one of the individual extending features 72a, 72b, 72c. Location of the target ostium 1014 may be carried out by endoscopic means alone. Alternatively, or in addition thereto, fluoroscopic visualization may be used to supplement or replace endoscopic visualization. Accordingly when only endoscopic visualization is used, this may eliminate the need for radio-opaque markings in some instances. When used, radio-opaque markings on the two outermost extending features 72c, help the user to locate the target ostium 1014 and also to visualize, by fluoroscopy, when the walls of the target ostium 1014 are in con tact with the outermost extending features 72c, 72c'. The telescoping ostium measuring devices 60 as with other embodiments of the invention are capable of measuring elliptical ostia by obtaining both the major and minor diameters of an oval target ostium.

The measuring device 60 may include flexible or malleable portions as well as semi-rigid or rigid portions. Such portions of the ostium measuring device 60 may be made from materials such as metallic tubes, rods (e.g. rods embedded in a shaft or wire. Suitable biocompatible material(s) that can be used for construction of an ostium measuring device in dude but are not limited to metals e.g. malleable stainless steel, fully annealed stainless steel, copper, aluminum, titanium, nickel-titanium alloy (e.g., Nitinol), etc.; polymers e.g. Pebax, PEEK, Nylon, polyethylene, etc, as described above.

Figure 6:
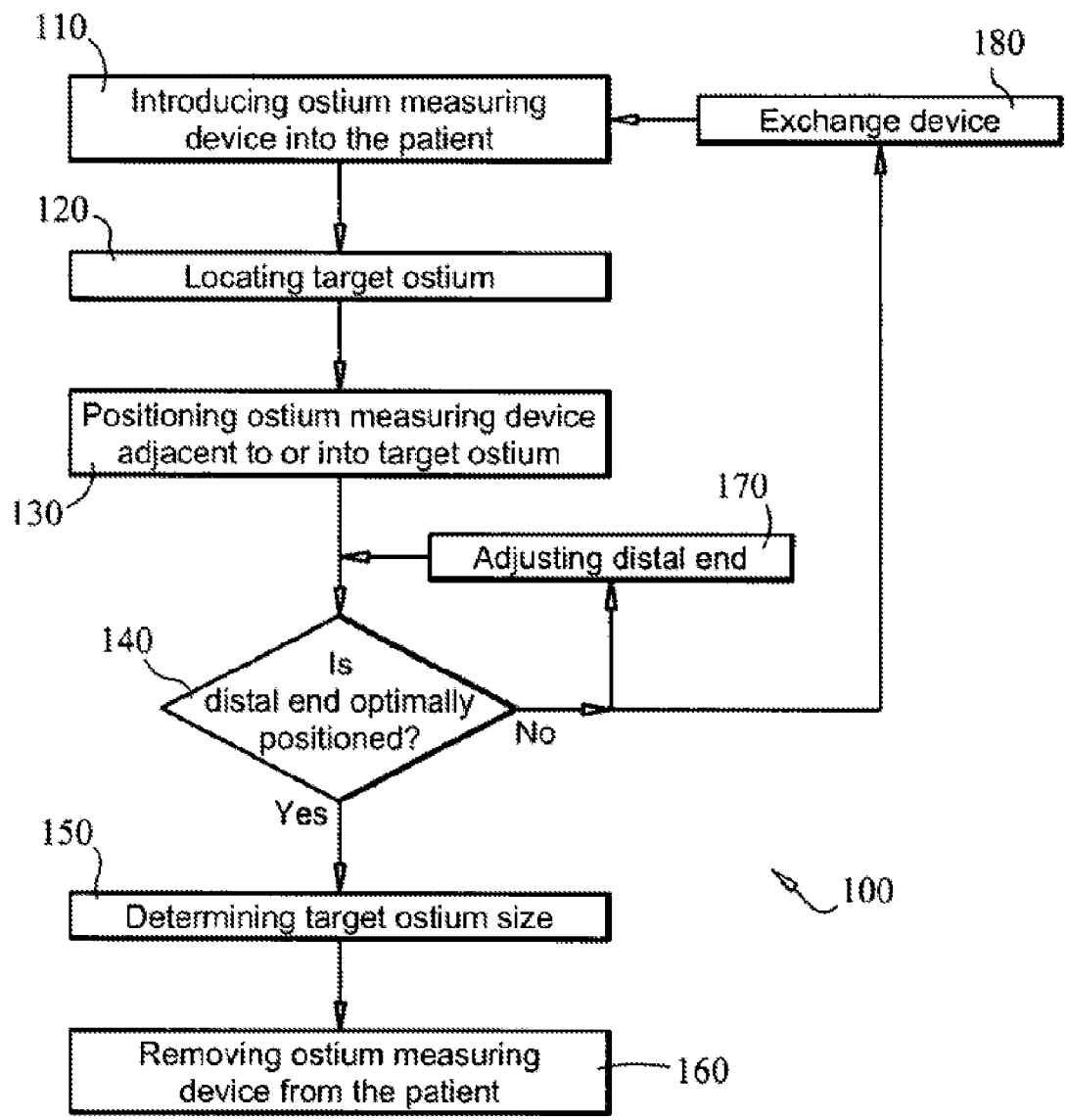
FIG. 6 is a flow chart showing a method for measuring an ostium in accordance with the invention.

Turning now to FIG. 6, there is shown is a flow chart of one embodiment 100 of the methods for measuring an ostium of a patient with an ostium measuring device in accordance with the invention. This method embodiment comprises; introducing an ostium measuring device within a patient 110, locating a target ostium with the ostium measuring device 120, positioning the ostium measuring device near or into the target ostium 130, and determining whether or not the distal end of the ostium measuring device is optimally positioned 140. For the devices shown in FIGS. 2, 4 and 5, the device is optimally placed when the fit between the device and the ostium is snug, but not excessively tight, so that the device becomes stuck or "hung up" on the ostium. For the device in FIG. 3, the device is optimally placed when the ribbon is flush against the plane of the ostium, somewhat like measuring with a measuring tape. If the distal end is optimally positioned in event 140, determining the size of the ostium by comparing the ostium to the ostium measuring device 150 is carried out, followed by removing the ostium measuring device from the patient 160. If the distal end is not optimally positioned in event 140, adjusting the distal end may be carried out, followed by repeating event 140. Alternatively, when the distal end is not optimally positioned, exchanging the ostium measuring device 180 may occur, followed by repeating of events 110 through 140.

Introducing the ostium measuring device into a patient 110 involves inserting the measuring device into an opening such as the throat, an ear or a nostril of a patient. The ostium measuring devices of the instant invention, as described above, comprise a distal end portion and proximal end portion, the distal end portion configured to easily fit into the opening of an ear, nostril or the throat. When the target ostium is a sinus ostium, the distal end portion of the ostium measuring device is inserted into a nostril either independently or with the aid of a secondary device such a guidewire or an illuminating guidewire as described in co-pending commonly assigned application Ser. No. 11/522,497 filed Sep. 15, 2006 and titled "Methods and Devices for Facilitating Visualization in a Surgical Environment," now U.S. Pat. No. 7,559,925, issued Jul. 14, 2009. Additionally, or alternatively, a sinus guide (e.g., guide catheter) may be used to facilitate placement of the measuring device close to the ostium of interest. application Ser. No. 11/522,497 is hereby incorporated herein, in its entirety, by reference thereto. In many embodiments of the invention introducing the ostium measuring device further comprises connecting a handpiece or guide catheter to the proximal end portion of the measuring device. A handpiece or guide catheter can aid the user in introducing the distal end portion of the measuring device into the patient as well as help mediate the advancement of the device through regions of the patient's body, such as the ear canal or nasal passageway.

Locating the target ostium 120 with the ostium measuring device may be performed with the use of visual navigation techniques or by physical familiarity of an ostium with the ostium measuring device by the user, with no need for any visualization equipment. When the method for measuring an ostium includes utilizing visual navigation equipment, the target ostium can be located by endoscopy equipment, fluoroscopy systems, X-ray imaging, image guided surgery (IGS) systems, or other visualization systems. Embodiments which utilize fluoroscopy or other x-ray techniques for locating the target ostium may further comprise visualizing at least one radio-opaque marker positioned on the distal end portion of the ostium measuring device as described above. Locating the target ostium in certain embodiments, such as when using the device shown in FIG. 4*c*, involve having the ostium measuring device connected to a guidewire already inserted through the target ostium.

Positioning the ostium measuring device correctly with relation to the target ostium 130 to make an ostium measurement, will vary depending on which embodiment of the ostium measuring device is being used. For embodiments such as those illustrated in FIGS. 2*a*, 2*b*, 4*a-c*, 5*a* and 5*c*, positioning the ostium measuring device comprises inserting a portion of the distal end portion of the measuring device into the target ostium. When the ostium measuring device comprises a spherical shaped tip on the distal end portion of the device as illustrated in FIGS. 2*a* and 2*b*, the device is correctly positioned 130 when the spherical portion of the device matches the diameter (e.g., contacts or closely approximates the walls) of the target ostium. For those embodiments where the distal end portion is a tapered mandrel, such as is shown in FIGS. 4*a-c*, positioning the measuring device correctly comprises inserting the tapered mandrel into the target ostium until the outer circumference of the distal end portion of the device contacts (or closely approximates) the walls of the target ostium. In the case of a telescoping measuring portion on the distal end portion, as shown in FIGS. 5*a* and 5*b*, the user places the central housing on the distal end portion within the target ostium and then, by adjusting the knob on the handpiece of the measuring device, extends the telescoping features of the telescoping portion until the outermost extending features touch (or closely approximate) the walls of the ositum.

In event 140, a decision is made by the surgeon as to whether or not the distal end of the ostium measuring device is optimally positioned with respect to the ostium to be measured. If yes, events 150 and 160 are carried out. If not, event 170 is carried out, followed by repetition of event 140. Alternatively, in certain embodiments event 180 is carried out, followed by repetition of events 110 through 140.

When the ostium measuring device comprises a spherical shaped tip on the distal end portion of the device as in the embodiments of FIG. 2*a* and FIG. 2*b*, the spherical portion of the distal end portion may easily slide through the target ostium, indicating that the ostium is larger than the diameter of the spherical portion. Or, the spherical portion may not fit through the target ostium, indicating the ostium is smaller than the diameter of spherical tip of the device. In this situation, exchanging the measuring device 180 is carried out, and the ostium measuring device is removed, and a new ostium measuring device is inserted, and steps 110 through 140 are repeated.

When the ostium measuring device includes a tapered mandrel distal end portion as shown in FIG. 4*a* through 4*c*, or a curvilinear distal end portion as shown in FIG. 3*a* and FIG. 3*b*, once the distal end portion is positioned in event 130, the determination of event 140 involves determination as to whether or not the distal end portion needs adjusting in step 170 by further extending or advancing, or alternatively withdrawing or retracting, the distal end portion, with respect to the ostium to be measured. Event 140 is then repeated after the adjusting.

In the embodiments of FIG. 5*a* and FIG. 5*b*, if the outermost telescoping features 72*c*, 72*c*' are not in contact with (or in sufficiently close approximation to, in the opinion of the surgeon) the ostium in event 140, an adjustment is made in event 170 by turning the knob on the handpiece to adjust the position of features 72*c*, 72*c*'. Event 140 is then repeated after the adjusting.

In event 150, determining or measuring the target ostium size is carried out. In the embodiments of FIG. 2*a* and FIG. 2*b*, when the spherical portion of the measuring device fits snugly into (or closely approximates) the target ostium, the diameter or size of the ostium is determined by measuring or verifying the diameter of the spherical distal end. For example, a 3.5 mm sphere may be passable through the ostium, while a 4 mm sphere may not be able to be passed therethrough. In such a case, a surgeon may make a judgment call as to whether the ostium is closer to 3.5 mm or 4 mm. Alternatively, the surgeon may interpolate the measurement to something in between 35 mm and 4 mm based on the surgeon's visualization of the process and judgment. Further alternatively, another set of devices 10 having smaller incremental size variations between 3.5 mm and 4 mm may be resorted to.

In embodiments of FIG. 3*a*, FIG. 3*b* and FIG. 4*a* through 4*c*, when the mandrel shaped or curvilinear distal end portion fits snugly within or over the ostium, the ostium diameter is measured by reading the indicia on the distal end portion, or by counting the radio-opaque and radio-transparent bands on the distal end portion. Radio-opaque markings on the distal end portions can be counted by the user and the diameter of the ostium can be determined by comparing the distance of the portion of the measuring device which crosses or overlays the diameter of the target ostium. For target ostia which have an oval shape, the ostium measuring device of FIGS. 3a and 3b can be oriented approximately 90 degrees across the ostium and another measurement can be taken, allowing both the major and minor diameters of the ostium to be determined.

In embodiments of FIG. 5a and FIG. 5b, when extensible features 72c, 72c' are in contact with the ostium, measurement is made by reading the indicia on the handpiece that are adjacent to the arrow on the adjustable knob. Oval ostia can be measured in similar fashion to that described above, e.g., by rotation of the distal end portion by about ninety degrees and taking another measurement.

Removing the ostium measuring device 150 from the patient comprises withdrawing the distal end portion and shaft of the measuring device from the ostium and nasal cavity through the patient's nostril.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for measuring the size of a paranasal sinus ostium of a patient, the method comprising the steps of:
   (a) inserting a distal end portion of a paranasal sinus ostium measuring device internally into a patient, locating the paranasal sinus ostium to be measured with the distal end portion of the paranasal sinus ostium measuring device;
   (b) positioning the distal end portion of the paranasal sinus ostium measuring device within the patient to enable the target paranasal sinus ostium to be measured;
   (c) determining the paranasal sinus ostium size of the targeted paranasal sinus ostium by the paranasal sinus ostium measuring device, wherein the act of determining the paranasal sinus ostium size comprises determining the diameter of the paranasal sinus ostium by identifying a diameter of a portion of the distal end portion of the paranasal sinus ostium measuring device which contacts or closely approximates the walls of the paranasal sinus ostium;
   (d) withdrawing the paranasal sinus ostium measuring device from the targeted paranasal sinus ostium;
   (e) subsequent to withdrawing the paranasal sinus ostium measuring device, selecting a dilator device based upon the determined size of the targeted paranasal sinus ostium; and
   (f) dilating the targeted paranasal sinus ostium with the selected dilator device, wherein the act of dilating comprises remodeling bony structure that surrounds or is adjacent to the targeted paranasal sinus ostium.

2. The method of claim 1, wherein the distal end portion comprises an atraumatic tip.

3. The method of claim 2, wherein the atraumatic tip is substantially spherical.

4. The method of claim 2, wherein the distal end portion comprises a tapered mandrel extending proximally from the atraumatic tip.

5. The method of claim 3, wherein the spherical atraumatic tip is configured to fit within a paranasal ostium.

6. The method of claim 5, wherein the diameter of the spherical tip is in a range of about 0.5 mm to about 6 mm.

7. The method of claim 3, wherein the substantially spherical atraumatic tip comprises a radio-opaque marker.

8. The method of claim 7, further comprising indicia visible on the radio-opaque marker.

9. The method of claim 3, wherein the diameter of the substantially spherical tip ranges from about 0.5 mm to about 6 mm.

10. The device method of claim 1, wherein the distal end portion is flexible and malleable.

11. The device method of claim 1, wherein a proximal end portion of the paranasal sinus ostium measuring device has at least one portion that is flexible and malleable.

12. The method of claim 11, further comprising attaching a handpiece to the proximal end portion.

13. The method of claim 11, further comprising receiving at least the proximal end portion in a guide catheter.

14. The method of claim 1, further comprising a radio-opaque marking on the distal end portion.

15. The method of claim 14, further comprising indicia on the radio-opaque marking.

16. The method of claim 1, further comprising a plurality of radio-opaque markings on the distal end portion.

17. The method of claim 1, wherein the distal end portion comprises a telescoping portion.

18. The method of claim 17, wherein the telescoping portion comprises a central housing and telescoping features extendable transverse to a longitudinal axis of the distal end portion.

19. The method of claim 18, further comprising driving, via a handpiece with an actuator, the telescoping portion to retract and extend the telescoping features.

20. The method of claim 1, wherein the distal end portion has a lumen therethrough.

21. The method of claim 20, further comprising inserting a guidewire within the patient prior to inserting the measuring device, and wherein the distal end portion of the measuring device is inserted along the guidewire.

22. The method of claim 21 wherein the guidewire is an illuminating guidewire.

23. The method of claim 20, wherein the sinus ostium measuring device is preloaded onto a guidewire, the method comprising inserting the guidewire and preloaded paranasal sinus ostium measuring device within the patient.

24. The method of claim 1, wherein a proximal end portion of said paranasal sinus ostium measuring device is configured to connect to a handpiece.

25. The method of claim 1, wherein a proximal end portion of the paranasal sinus ostium measuring device is configured to connect to a guide catheter.

26. A method for measuring the size of a paranasal sinus ostium of a patient, the method comprising the steps of:
   (a) inserting a distal end portion of a paranasal sinus ostium measuring device internally into a patient, locating the paranasal sinus ostium to be measured with the distal end portion of the paranasal sinus ostium measuring device;

(b) positioning the distal end portion of the paranasal sinus ostium measuring device within the patient to enable the target paranasal sinus ostium to be measured;

(c) determining the paranasal sinus ostium size of the targeted paranasal sinus ostium by the paranasal sinus ostium measuring device, wherein the act of determining the paranasal sinus ostium size comprises determining the diameter of the paranasal sinus ostium by identifying a diameter of a portion of the distal end portion of the paranasal sinus ostium measuring device which contacts or closely approximates the walls of the paranasal sinus ostium, wherein the portion of the distal end portion of the paranasal sinus ostium measuring device which contacts the walls of the paranasal sinus ostium is a tapered mandrel including a proximal portion and a distal end, the distal end having a tip, the tip being narrower in width than the proximal portion;

(d) withdrawing the paranasal sinus ostium measuring device from the targeted paranasal sinus ostium;

(e) subsequent to withdrawing the paranasal sinus ostium measuring device, selecting a dilator device based upon the determined size of the targeted paranasal sinus ostium; and (f) dilating the targeted paranasal sinus ostium with the selected dilator device, wherein the act of dilating comprises remodeling bony structure that surrounds or is adjacent to the targeted paranasal sinus ostium.

27. A method for measuring the size of a paranasal sinus ostium of a patient, the method comprising the steps of:

(a) inserting a distal end portion of a paranasal sinus ostium measuring device internally into a patient, locating the paranasal sinus ostium to be measured with the distal end portion of the paranasal sinus ostium measuring device;

(b) positioning the distal end portion of the paranasal sinus ostium measuring device within the patient to enable the target paranasal sinus ostium to be measured;

(c) determining the paranasal sinus ostium size of the targeted paranasal sinus ostium by the paranasal sinus ostium measuring device, wherein the act of determining the paranasal sinus ostium size comprises determining the diameter of the paranasal sinus ostium by identifying a diameter of a portion of the distal end portion of the paranasal sinus ostium measuring device which contacts or closely approximates the walls of the paranasal sinus ostium, wherein the portion of the distal end portion of the paranasal sinus ostium measuring device which contacts the walls of the paranasal sinus ostium comprises a substantially spherical atraumatic tip;

(d) withdrawing the paranasal sinus ostium measuring device from the targeted paranasal sinus ostium;

(e) subsequent to withdrawing the paranasal sinus ostium measuring device, selecting a dilator device based upon the determined size of the targeted paranasal sinus ostium; and (f) dilating the targeted paranasal sinus ostium with the selected dilator device, wherein the act of dilating comprises remodeling bony structure that surrounds or is adjacent to the targeted paranasal sinus ostium.

* * * * *